(12) United States Patent
Fang et al.

(10) Patent No.: US 12,203,059 B2
(45) Date of Patent: Jan. 21, 2025

(54) MICROWELL DESIGN AND FABRICATION FOR GENERATION OF CELL CULTURE AGGREGATES

(71) Applicant: CORNING INCORPORATED, Corning, NY (US)

(72) Inventors: Ye Fang, Painted Post, NY (US); Ann MeeJin Ferrie, Salem, NH (US); Vasiliy Nikolaevich Goral, Painted Post, NY (US); Allison Jean Tanner, Portsmouth, NH (US); Qi Wu, Painted Post, NY (US)

(73) Assignee: CORNING INCORPORATED, Corning, NY (US)

( * ) Notice: Subject to any disclaimer, the term of this patent is extended or adjusted under 35 U.S.C. 154(b) by 0 days.

(21) Appl. No.: 17/532,196

(22) Filed: Nov. 22, 2021

(65) Prior Publication Data
US 2022/0081661 A1 Mar. 17, 2022

Related U.S. Application Data

(63) Continuation of application No. 15/499,370, filed on Apr. 27, 2017, now abandoned, which is a continuation of application No. PCT/US2015/058123, filed on Oct. 29, 2015.

(60) Provisional application No. 62/072,019, filed on Oct. 29, 2014.

(51) Int. Cl.
*C12M 1/00* (2006.01)
*C12M 1/32* (2006.01)
*C12M 1/34* (2006.01)
*C12N 5/00* (2006.01)

(52) U.S. Cl.
CPC ............ *C12M 23/12* (2013.01); *C12M 41/36* (2013.01); *C12N 5/0062* (2013.01)

(58) Field of Classification Search
CPC ...... C12M 23/12; C12M 41/36; C12N 5/0062
See application file for complete search history.

(56) References Cited

U.S. PATENT DOCUMENTS

| 2,947,116 A | 8/1960 | Wilton et al. |
| 3,630,849 A | 12/1971 | David et al. |
| 4,382,685 A | 5/1983 | Pearson |

(Continued)

FOREIGN PATENT DOCUMENTS

| AU | 2004256209 A1 | 1/2005 |
| CA | 2558946 A1 | 1/2005 |

(Continued)

OTHER PUBLICATIONS

"Identification grid for microplates", Rtreived from: https://www.kisker-biotech.com/frontoffice/product?produitId=0N-27-11, 2 pages, 2021.

(Continued)

*Primary Examiner* — Lydia Edwards
(74) *Attorney, Agent, or Firm* — Chandra J. Duncan

(57) ABSTRACT

A cell culture apparatus may include a substrate defining a well. The well may define an interior surface, an exterior surface, an upper aperture and a nadir. The substrate may define a thickness between the interior and exterior surfaces that has a thickness proximate the nadir that is greater than or equal to a thickness proximate the upper aperture.

12 Claims, 7 Drawing Sheets

(56) References Cited

U.S. PATENT DOCUMENTS

| | | |
|---|---|---|
| 4,498,785 A | 2/1985 | De Bruyne |
| 4,534,656 A | 8/1985 | De Bruyne |
| 4,670,396 A | 6/1987 | Bear et al. |
| 4,760,028 A | 7/1988 | De Bruyne et al. |
| 4,927,764 A | 5/1990 | Lyman et al. |
| 4,980,293 A | 12/1990 | Jeffs |
| 5,047,347 A | 9/1991 | Cline |
| 5,151,366 A | 9/1992 | Serkes et al. |
| 5,171,994 A | 12/1992 | Bahraman |
| 5,171,995 A | 12/1992 | Gast et al. |
| 5,240,854 A | 8/1993 | Berry et al. |
| 5,272,084 A | 12/1993 | O'Connell et al. |
| 5,319,436 A | 6/1994 | Manns et al. |
| 5,374,557 A | 12/1994 | Verma |
| 5,398,837 A | 3/1995 | Degrassi |
| 5,487,872 A | 1/1996 | Hafeman et al. |
| 5,554,536 A | 9/1996 | Rising |
| 5,598,262 A | 1/1997 | Jutard et al. |
| 5,665,562 A | 9/1997 | Cook |
| 5,693,537 A | 12/1997 | Wilson et al. |
| 5,707,869 A | 1/1998 | Wolf et al. |
| 5,710,043 A | 1/1998 | Pay |
| 5,736,397 A | 4/1998 | Garcia et al. |
| 5,759,494 A | 6/1998 | Szlosek |
| 5,766,949 A | 6/1998 | Liau et al. |
| 5,772,905 A | 6/1998 | Chou |
| 5,783,440 A | 7/1998 | Stevens |
| 5,792,653 A | 8/1998 | Weibezahn et al. |
| 5,858,309 A | 1/1999 | Mathus et al. |
| 5,972,694 A | 10/1999 | Mathus |
| 6,030,829 A | 2/2000 | Dannoux et al. |
| 6,039,972 A | 3/2000 | Barlow et al. |
| 6,306,646 B1 | 10/2001 | Saad et al. |
| 6,348,999 B1 | 2/2002 | Summersgill et al. |
| 6,514,464 B1 | 2/2003 | Knebel |
| 6,521,451 B2 | 2/2003 | Potter |
| 6,567,675 B1 | 5/2003 | Rosen et al. |
| 6,767,607 B2 | 7/2004 | Tanner et al. |
| 6,811,752 B2 | 11/2004 | Barbera-Guillem |
| 6,908,767 B2 | 6/2005 | Bader |
| 7,470,424 B2 | 12/2008 | Kataoka et al. |
| 7,547,547 B2 | 6/2009 | Dang et al. |
| 7,674,346 B2 | 3/2010 | Clements et al. |
| 7,687,262 B2 | 3/2010 | Cattadoris |
| 7,691,369 B2 | 4/2010 | Kataoka et al. |
| 7,727,759 B2 | 6/2010 | Ozawa et al. |
| 7,745,209 B2 | 6/2010 | Martin et al. |
| 7,745,210 B2 | 6/2010 | Martin |
| 7,897,379 B2 | 3/2011 | Kenney et al. |
| 7,919,319 B2 | 4/2011 | Jervis et al. |
| 8,053,230 B2 | 11/2011 | Whittlinger |
| 8,143,053 B2 | 3/2012 | Yerbic |
| 8,148,152 B2 | 4/2012 | Kolossov et al. |
| 8,158,426 B2 | 4/2012 | Wilson et al. |
| 8,158,427 B2 | 4/2012 | Wilson et al. |
| 8,163,537 B2 | 4/2012 | Martin et al. |
| 8,168,432 B2 | 5/2012 | Wilson et al. |
| 8,178,345 B2 | 5/2012 | Bennett et al. |
| 8,273,572 B2 | 9/2012 | Martin et al. |
| 8,318,479 B2 | 11/2012 | Domansky et al. |
| 8,415,144 B2 | 4/2013 | Wilson et al. |
| 8,470,589 B2 | 6/2013 | Martin et al. |
| D685,497 S | 7/2013 | Kenney et al. |
| 8,486,692 B2 | 7/2013 | Simon |
| 8,597,597 B2 | 12/2013 | Deutsch et al. |
| 8,617,879 B2 | 12/2013 | Yu et al. |
| 8,697,443 B2 | 4/2014 | Wilson et al. |
| 8,759,017 B2 | 6/2014 | Owen et al. |
| 8,778,669 B2 | 7/2014 | Lacey et al. |
| 8,846,399 B2 | 9/2014 | Martin et al. |
| 8,906,685 B2 | 12/2014 | Takayama et al. |
| 8,932,544 B2 | 1/2015 | Mueller et al. |
| 9,039,883 B2 | 5/2015 | Guerrieri et al. |
| 9,040,293 B2 | 5/2015 | Gulzow et al. |
| 9,045,721 B2 | 6/2015 | Martin et al. |
| 9,068,281 B2 | 6/2015 | Wu et al. |
| 9,126,199 B2 | 9/2015 | Moritz et al. |
| 9,169,460 B2 | 10/2015 | Cecchi |
| D748,812 S | 2/2016 | Kenney et al. |
| 9,260,684 B1 | 2/2016 | Egeler et al. |
| 9,260,695 B2 | 2/2016 | Crowley et al. |
| 9,493,733 B2 | 11/2016 | Giles |
| 9,494,577 B2 | 11/2016 | McGarr et al. |
| 9,573,128 B1 | 2/2017 | McClelland |
| 9,587,213 B2 | 3/2017 | Morgan et al. |
| 9,636,680 B2 | 5/2017 | Fattinger et al. |
| 9,732,317 B2 | 8/2017 | Wilson |
| 9,790,465 B2 | 10/2017 | Bennett et al. |
| 9,845,451 B2 | 12/2017 | Martin et al. |
| 9,862,918 B2 | 1/2018 | Ito |
| 10,254,274 B2 | 4/2019 | Miklas et al. |
| 11,441,121 B2 | 9/2022 | Bennett et al. |
| 11,613,722 B2 | 3/2023 | Martin et al. |
| 2002/0022219 A1 | 2/2002 | Clements et al. |
| 2002/0172621 A1 | 11/2002 | Barbera-Guillem |
| 2003/0031829 A1 | 2/2003 | Tanner et al. |
| 2003/0104494 A1 | 6/2003 | Ravkin et al. |
| 2003/0183958 A1 | 10/2003 | Goff et al. |
| 2003/0186217 A1 | 10/2003 | Bader |
| 2003/0215941 A1 | 11/2003 | Campbell et al. |
| 2004/0091397 A1 | 5/2004 | Picard |
| 2004/0101955 A1 | 5/2004 | Whitley |
| 2004/0125266 A1 | 7/2004 | Miyauchi et al. |
| 2004/0216835 A1 | 11/2004 | Tanner et al. |
| 2004/0259242 A1 | 12/2004 | Malinge et al. |
| 2004/0259423 A1 | 12/2004 | Elbaz et al. |
| 2005/0032208 A1 | 2/2005 | Oh et al. |
| 2005/0047971 A1 | 3/2005 | Clements et al. |
| 2005/0052646 A1* | 3/2005 | Wohlstadter .............. B01L 9/50 356/311 |
| 2005/0074873 A1 | 4/2005 | Shanler et al. |
| 2005/0112030 A1 | 5/2005 | Gaus |
| 2005/0116717 A1 | 6/2005 | Dransfield et al. |
| 2005/0147959 A1 | 7/2005 | Frondoza et al. |
| 2006/0110822 A1 | 5/2006 | Robbins et al. |
| 2006/0234370 A1 | 10/2006 | Korpinen et al. |
| 2006/0252044 A1 | 11/2006 | Okumura et al. |
| 2006/0292654 A1 | 12/2006 | Reardon |
| 2007/0178441 A1 | 8/2007 | Li |
| 2007/0216897 A1 | 9/2007 | Sonda |
| 2008/0003671 A1 | 1/2008 | Martin |
| 2008/0009027 A1 | 1/2008 | Fraker et al. |
| 2008/0118974 A1 | 5/2008 | Martin et al. |
| 2008/0206857 A1 | 8/2008 | Kenney et al. |
| 2008/0268515 A1 | 10/2008 | Cullimore et al. |
| 2008/0297784 A1 | 12/2008 | Leblanc et al. |
| 2008/0299649 A1 | 12/2008 | Martin et al. |
| 2008/0300278 A1 | 12/2008 | Torrens et al. |
| 2009/0017540 A1 | 1/2009 | Nishio et al. |
| 2009/0018033 A1 | 1/2009 | Morgan et al. |
| 2009/0029462 A1 | 1/2009 | Beardsley et al. |
| 2009/0037293 A1 | 2/2009 | Unger et al. |
| 2009/0170190 A1 | 7/2009 | Nishi et al. |
| 2009/0191620 A1 | 7/2009 | Martin et al. |
| 2009/0288963 A1 | 11/2009 | Guerrieri et al. |
| 2009/0298164 A1 | 12/2009 | Cattadoris et al. |
| 2009/0298166 A1 | 12/2009 | Fang et al. |
| 2010/0055774 A1 | 3/2010 | Wilson |
| 2010/0068793 A1 | 3/2010 | Ungrin et al. |
| 2010/0093075 A1 | 4/2010 | Mueller |
| 2010/0112014 A1 | 5/2010 | Gilbert et al. |
| 2010/0112684 A1 | 5/2010 | Lee et al. |
| 2010/0119418 A1 | 5/2010 | Clements et al. |
| 2010/0170790 A1 | 7/2010 | Takahashi et al. |
| 2010/0190197 A1 | 7/2010 | Martin et al. |
| 2010/0197013 A1 | 8/2010 | Kamp et al. |
| 2010/0247386 A1 | 9/2010 | Deutsch et al. |
| 2010/0273258 A1 | 10/2010 | Lannutti et al. |
| 2010/0297600 A1 | 11/2010 | Cecchi |
| 2011/0086375 A1 | 4/2011 | Ungrin et al. |
| 2011/0097790 A1 | 4/2011 | Yerbic |
| 2011/0129923 A1 | 6/2011 | Wilson et al. |
| 2011/0229961 A1 | 9/2011 | Higashi et al. |
| 2012/0064627 A1 | 3/2012 | Khine et al. |

(56) References Cited

U.S. PATENT DOCUMENTS

| | | |
|---|---|---|
| 2012/0129208 A1 | 5/2012 | Khine et al. |
| 2012/0129257 A1 | 5/2012 | Yu et al. |
| 2012/0219572 A1 | 8/2012 | Prockop et al. |
| 2013/0052331 A1 | 2/2013 | Kram et al. |
| 2013/0122539 A1 | 5/2013 | Li et al. |
| 2013/0122580 A1 | 5/2013 | Tsukada et al. |
| 2013/0143254 A1 | 6/2013 | Thomas et al. |
| 2013/0164848 A1 | 6/2013 | Munaka et al. |
| 2013/0203159 A1 | 8/2013 | Itoh et al. |
| 2013/0344598 A1 | 12/2013 | Nistor |
| 2014/0004086 A1 | 1/2014 | Peak |
| 2014/0027784 A1 | 1/2014 | Wada et al. |
| 2014/0099717 A1 | 4/2014 | Fraker et al. |
| 2014/0106394 A1 | 4/2014 | Ko et al. |
| 2014/0106452 A1 | 4/2014 | Vukasinovic |
| 2014/0120573 A1 | 5/2014 | Tavana et al. |
| 2014/0178992 A1 | 6/2014 | Nakashima et al. |
| 2014/0221225 A1 | 8/2014 | Danen et al. |
| 2014/0226004 A1 | 8/2014 | Son et al. |
| 2014/0227784 A1 | 8/2014 | Ejiri et al. |
| 2014/0315296 A1 | 10/2014 | Wilson |
| 2014/0322806 A1 | 10/2014 | Bennett et al. |
| 2015/0004686 A1 | 1/2015 | Goral et al. |
| 2015/0064738 A1 | 3/2015 | Tsukada et al. |
| 2015/0072405 A1 | 3/2015 | Ito |
| 2015/0184119 A1 | 7/2015 | Tsukada et al. |
| 2015/0247112 A1 | 9/2015 | Orr et al. |
| 2016/0003796 A1 | 1/2016 | Kranbuehl |
| 2016/0017267 A1 | 1/2016 | Hansen et al. |
| 2016/0040120 A1 | 2/2016 | Gottwald et al. |
| 2016/0137962 A1 | 5/2016 | Ejiri et al. |
| 2016/0194588 A1 | 7/2016 | Guenat et al. |
| 2016/0216250 A1 | 7/2016 | Ritter et al. |
| 2016/0250631 A1 | 9/2016 | Kang et al. |
| 2017/0067019 A1 | 3/2017 | Ho |
| 2017/0073625 A1 | 3/2017 | Kasuto et al. |
| 2017/0226455 A1 | 8/2017 | Fang et al. |
| 2017/0267959 A1 | 9/2017 | Martin et al. |
| 2017/0283757 A1 | 10/2017 | Carter et al. |
| 2017/0306281 A1 | 10/2017 | Martin et al. |
| 2017/0342363 A1 | 11/2017 | Fang et al. |
| 2018/0166743 A1 | 6/2018 | Lee et al. |
| 2018/0201888 A1 | 7/2018 | Miwa et al. |
| 2018/0301754 A1 | 10/2018 | Badding et al. |
| 2019/0006707 A1 | 1/2019 | Sakamoto et al. |
| 2020/0131461 A1 | 4/2020 | Martin et al. |
| 2020/0199006 A1 | 6/2020 | Jain et al. |
| 2020/0239854 A1 | 7/2020 | Ayano et al. |
| 2021/0062126 A1 | 3/2021 | Martin et al. |
| 2022/0220434 A1 | 7/2022 | Martin et al. |

FOREIGN PATENT DOCUMENTS

| | | |
|---|---|---|
| CA | 2679011 A1 | 9/2008 |
| CA | 2848875 A1 | 3/2013 |
| CN | 2186755 Y | 1/1995 |
| CN | 1168921 A | 12/1997 |
| CN | 1234112 A | 11/1999 |
| CN | 1867663 A | 11/2006 |
| CN | 1875093 A | 12/2006 |
| CN | 201626959 U | 11/2010 |
| CN | 101978041 A | 2/2011 |
| CN | 102105578 A | 6/2011 |
| CN | 102257123 A | 11/2011 |
| CN | 102449135 A | 5/2012 |
| CN | 102687023 A | 9/2012 |
| CN | 202450098 U | 9/2012 |
| CN | 202849407 U | 4/2013 |
| CN | 103080294 A | 5/2013 |
| CN | 103119151 A | 5/2013 |
| CN | 203513696 U | 4/2014 |
| CN | 103814125 A | 5/2014 |
| CN | 204608026 U | 9/2015 |
| CN | 204702760 U | 10/2015 |
| CN | 204714819 U | 10/2015 |
| CN | 204752742 U | 11/2015 |
| CN | 204803327 U | 11/2015 |
| CN | 205170866 U | 4/2016 |
| CN | 205669029 U | 11/2016 |
| CN | 205839030 U | 12/2016 |
| CN | 205990396 U | 3/2017 |
| CN | 107208025 A | 9/2017 |
| CN | 107460125 A | 12/2017 |
| DE | 8309876 U1 | 12/1983 |
| DE | 10019862 A1 | 11/2001 |
| DE | 202006017853 U1 | 1/2007 |
| DE | 102009005526 A1 | 7/2010 |
| DE | 102014214077 A1 | 1/2016 |
| DE | 102014017728 A1 | 6/2016 |
| EP | 0307048 A2 | 3/1989 |
| EP | 0605527 A1 | 7/1994 |
| EP | 0681846 A2 | 11/1995 |
| EP | 0800571 A2 | 10/1997 |
| EP | 0834552 A1 | 4/1998 |
| EP | 0965633 A1 | 12/1999 |
| EP | 1181349 A1 | 2/2002 |
| EP | 1348533 A2 | 10/2003 |
| EP | 1445022 A2 | 8/2004 |
| EP | 1988152 A1 | 11/2008 |
| EP | 2032262 A2 | 3/2009 |
| EP | 2617807 A1 | 7/2013 |
| EP | 2653531 A1 | 10/2013 |
| EP | 2759592 A1 | 7/2014 |
| EP | 2896684 A1 | 7/2015 |
| EP | 3081627 A1 | 10/2016 |
| EP | 3296018 A1 | 3/2018 |
| EP | 3351615 A1 | 7/2018 |
| EP | 3372666 A1 | 9/2018 |
| GB | 2147100 A | 5/1985 |
| JP | 03-139350 A | 6/1991 |
| JP | 06-038734 A | 2/1994 |
| JP | 06-327462 A | 11/1994 |
| JP | 09-173049 A | 7/1997 |
| JP | 09-234811 A | 9/1997 |
| JP | 10-210866 A | 8/1998 |
| JP | 10-210966 A | 8/1998 |
| JP | 2001-106749 A | 4/2001 |
| JP | 2003-135056 A | 5/2003 |
| JP | 2003-180335 A | 7/2003 |
| JP | 2004-129558 A | 4/2004 |
| JP | 2004-535829 A | 12/2004 |
| JP | 2005-080660 A | 3/2005 |
| JP | 2006-121991 A | 5/2006 |
| JP | 2006-191809 A | 7/2006 |
| JP | 2007-510429 A | 4/2007 |
| JP | 3139350 U | 2/2008 |
| JP | 2009-017810 A | 1/2009 |
| JP | 2009-050194 A | 3/2009 |
| JP | 2009-183288 A | 8/2009 |
| JP | 2009-542230 A | 12/2009 |
| JP | 2010-088347 A | 4/2010 |
| JP | 2010-104327 A | 5/2010 |
| JP | 2010-518879 A | 6/2010 |
| JP | 2010-158214 A | 7/2010 |
| JP | 2011-509686 A | 3/2011 |
| JP | 2011-521642 A | 7/2011 |
| JP | 2011-172533 A | 9/2011 |
| JP | 2011-528226 A | 11/2011 |
| JP | 2012-249547 A | 12/2012 |
| JP | 2013-055911 A | 3/2013 |
| JP | 2014-132869 A | 7/2014 |
| JP | 2015-012827 A | 1/2015 |
| JP | 2015-029431 A | 2/2015 |
| JP | 2015-073520 A | 4/2015 |
| JP | 2016-002023 A | 1/2016 |
| JP | 5845185 B2 | 1/2016 |
| JP | 2016-093149 A | 5/2016 |
| JP | 2016-136920 A | 8/2016 |
| JP | 2016-136921 A | 8/2016 |
| JP | 2017-532970 A | 11/2017 |
| JP | 2018-108032 A | 7/2018 |
| KR | 10-2014-0113139 A | 9/2014 |
| KR | 10-2014-0125662 A | 10/2014 |
| KR | 10-2017-0008539 A | 1/2017 |

(56) References Cited

FOREIGN PATENT DOCUMENTS

| | | |
|---|---|---|
| WO | 92/07063 A2 | 4/1992 |
| WO | 93/07258 A1 | 4/1993 |
| WO | 96/21851 A2 | 7/1996 |
| WO | 98/15355 A2 | 4/1998 |
| WO | 98/31466 A1 | 7/1998 |
| WO | 01/80997 A1 | 11/2001 |
| WO | 01/92462 A1 | 12/2001 |
| WO | 2004/044120 A2 | 5/2004 |
| WO | 2004/094060 A1 | 11/2004 |
| WO | 2005/047464 A2 | 5/2005 |
| WO | 2006/043267 A1 | 4/2006 |
| WO | 2007/015770 A1 | 2/2007 |
| WO | 2007/097120 A1 | 8/2007 |
| WO | 2008/006104 A2 | 1/2008 |
| WO | 2008/008149 A2 | 1/2008 |
| WO | 2008/106771 A1 | 9/2008 |
| WO | 2008/118500 A1 | 10/2008 |
| WO | 2008/140295 A1 | 11/2008 |
| WO | 2008/149039 A2 | 12/2008 |
| WO | 2008/153783 A1 | 12/2008 |
| WO | 2009/094125 A2 | 7/2009 |
| WO | 2009/148509 A1 | 12/2009 |
| WO | 2009/148512 A2 | 12/2009 |
| WO | 2010/008566 A2 | 1/2010 |
| WO | 2010/042072 A1 | 4/2010 |
| WO | 2010/069589 A1 | 6/2010 |
| WO | 2012/036011 A1 | 3/2012 |
| WO | 2012/077683 A1 | 6/2012 |
| WO | 2012/170232 A1 | 12/2012 |
| WO | 2013/042360 A1 | 3/2013 |
| WO | 2013/108293 A1 | 7/2013 |
| WO | 2013/116449 A1 | 8/2013 |
| WO | 2014/042162 A1 | 3/2014 |
| WO | 2014/072432 A1 | 5/2014 |
| WO | 2014/140181 A1 | 9/2014 |
| WO | 2014/156455 A1 | 10/2014 |
| WO | 2014/165273 A1 | 10/2014 |
| WO | 2014/171782 A1 | 10/2014 |
| WO | 2014/179196 A1 | 11/2014 |
| WO | 2014/196204 A1 | 12/2014 |
| WO | 2015/033507 A1 | 3/2015 |
| WO | 2015/061907 A1 | 5/2015 |
| WO | 2015/087369 A1 | 6/2015 |
| WO | 2016/020992 A1 | 2/2016 |
| WO | 2016/064757 A1 | 4/2016 |
| WO | 2016/069885 A1 | 5/2016 |
| WO | 2016/069892 A1 | 5/2016 |
| WO | 2016/069895 A1 | 5/2016 |
| WO | 2016/069917 A1 | 5/2016 |
| WO | 2016/069930 A1 | 5/2016 |
| WO | 2016/157322 A1 | 10/2016 |
| WO | 2017/025584 A1 | 2/2017 |
| WO | 2017/047735 A1 | 3/2017 |
| WO | 2017/077163 A1 | 5/2017 |
| WO | WO 2017/077163 | 5/2017 |
| WO | 2017/142410 A1 | 8/2017 |
| WO | 2018/068034 A1 | 4/2018 |
| WO | 2018/200893 A1 | 11/2018 |
| WO | 2019/010401 A1 | 1/2019 |
| WO | 2019/014621 A1 | 1/2019 |
| WO | 2019/014627 A1 | 1/2019 |
| WO | 2019/014635 A1 | 1/2019 |
| WO | 2019/014636 A1 | 1/2019 |
| WO | 2019/178039 A1 | 9/2019 |

OTHER PUBLICATIONS

International Preliminary Report on Patentability of the International Searching Authority; PCT/US2015/058053; Mailed May 11, 2017; 9 Pages; European Patent Office.

International Preliminary Report on Patentability of the International Searching Authority; PCT/US14/35635; Mailed Nov. 12, 2015; 9 Pages; European Patent Office.

International Preliminary Report on Patentability of the International Searching Authority; PCT/US15/58032; Mailed May 11, 2017; 7 Pages; European Patent Office.

International Preliminary Report on Patentability of the International Searching Authority; PCT/US15/58048; Mailed May 11, 2017; 9 Pages; European Patent Office.

International Preliminary Report on Patentability of the International Searching Authority; PCT/US15/58106; Mailed May 11, 2017; 8 Pages; European Patent Office.

International Preliminary Report on Patentability of the International Searching Authority; PCT/US2015/058123; Mailed May 11, 2017; 8 Pages; European Patent Office.

International Preliminary Report on Patentability of the International Searching Authority; PCT/US2018/042115; Mailed Jan. 23, 2020; 9 Pages; European Patent Office.

International Preliminary Report on Patentability of the International Searching Authority; PCT/US2018/042133; Mailed Jan. 23, 2020; 8 Pages; European Patent Office.

International Preliminary Report on Patentability of the International Searching Authority; PCT/US2018/042145; Mailed Jan. 23, 2020; 9 Pages; European Patent Office.

International Preliminary Report on Patentability of the International Searching Authority; PCT/US2018/042159; Mailed Jan. 23, 2020; 8 Pages; European Patent Office.

International Preliminary Report on Patentability of the International Searching Authority; PCT/US2018/042161; Mailed Jan. 23, 2020; 9 Pages.

International Search Report and Written of the International Searching Authority; PCT/US2018/042145; Mailed Oct. 26, 2018; 12 Pages; European Patent Office.

International Search Report and Written of the International Searching Authority; PCT/US2018/042159; Mailed Oct. 22, 2018; 10 Pages; European Patent Office.

International Search Report and Written Opinion of the International Searching Authority; PCT/US2021/044259; dated Nov. 8, 2021; 10 pages; Korean Patent Office.

International Search Report and Written Opinion of the International Searching Authority; PCT/US14/35635; Mailed Aug. 22, 2014; 9 Pages; European Patent Office.

International Search Report and Written Opinion of the International Searching Authority; PCT/US15/58032; Mailed Jan. 27, 2016; 9 Pages; European Patent Office.

International Search Report and Written Opinion of the International Searching Authority; PCT/US15/58048; Mailed Feb. 11, 2016; 11 Pages; European Patent Office.

International Search Report and Written Opinion of the International Searching Authority; PCT/US15/58106; Mailed Jan. 21, 2016; 9 Pages; European Patent Office.

International Search Report and Written Opinion of the International Searching Authority; PCT/US2015/058053; Mailed Jan. 20, 2016; 11 Pages; European Patent Office.

International Search Report and Written Opinion of the International Searching Authority; PCT/US2015/058123; Mailed Jan. 19, 2016; 9 Pages; European Patent Office.

International Search Report and Written Opinion of the International Searching Authority; PCT/US2018/041974; Mailed Mar. 14, 2019; 10 Pages; European Patent Office.

International Search Report and Written Opinion of the International Searching Authority; PCT/US2018/041985; Mailed Mar. 19, 2019; 11 Pages.

International Search Report and Written Opinion of the International Searching Authority; PCT/US2018/042004; Mailed Apr. 4, 2019; 10 Pages; European Patent Office.

International Search Report and Written Opinion of the International Searching Authority; PCT/US2018/042115; Mailed Oct. 16, 2018; 12 Pages; European Patent Office.

International Search Report and Written Opinion of the International Searching Authority; PCT/US2018/042133; Mailed Oct. 24, 2018; 11 Pages; European Patent Office.

International Search Report and Written Opinion of the International Searching Authority; PCT/US2018/042161; Mailed Dec. 12, 2018; 12 Pages; European Patent Office.

(56) References Cited

OTHER PUBLICATIONS

International Search Report and Written Opinion of the International Searching Authority; PCT/US2020/034120; mailed on Aug. 5, 2020, 15 pages; European Patent Office.
International Search Report and Written Opinion of the International Searching Authority; PCT/US2021/059622; mailed on May 23, 2022, 11 pages; European Patent Office.
Japanese Patent Application No. 2016-511776, Office Action Dated Feb. 15, 2018, 6 Pages; Japanese Patent Office.
Japanese Patent Application No. 2016-511776, Office Action Dated Jan. 17, 2019, 6 Pages; Japanese Patent Office.
Japanese Patent Application No. 2017-523816 Decision of Refusal dated Sep. 16, 2020; 11 Pages; Japanese Patent Office.
Japanese Patent Application No. 2019-215684 Office Action dated Jan. 27, 2021, 8 pages (4 pages of English Translation and 4 pages of Original Document); Japanese Patent Office.
Jeon et al, "Combined Effects of Flow-Induced Shear Stress and Micropatterned Surface Morphology on Neuronal Differentiation of Human Mesenchymal Stem Cells" J Biosci Bioeng, 2014, 117(2):242-247.
Jiang et al, "Shear Enhances Thrombopoiesis and Formation of Microparticles That Induce Megakaryocytic Differentiation of Stem Cells", Blood, Sep. 25, 2014; 124(13):2094-2103.
Junji Fukuda et al., "Hepatocyte Spheroid Arrays Inside Microwells Connected With Microchannels", Biomicrofluidics 5, 2011, pp. 10.
Kelm et al, "Method for generation of homogeneous multicellular tumor spheroids applicable to a wide variety of cell types", Biotechnology and Bioengineering 2003; 83(2):173-180.
Kim et al, "Shear Stress Induced by an Interstitial Level of Slow Flow Increases the Osteogenic Differentiation of Mesenchymal Stem Cells Through TAZ Activation" PloS ONE, Mar. 21, 2014; 9(3), e92427, 9 pages.
Koide et al., "Formation of multicellular spheroids composed of adult rat hepatocytes in dishes with positively charged surfaces and under other nonadherent environments", Exp Cell Res 1990; 186:227-235.
Kutsuzawa et al, "Highly Robust Protein Production by Co-Culture of CHO Spheroids Layered on Feeder Cells in Serum-Free Medium"; Colloid Polym Sci (2014) 292; 839-848.
Labusca, "Scaffold free 3D culture of mesenchymal stem cells; implications for regenerative medicine", J Transplant Stem Cel Biol 2015 2(1): 8.
Landry et al., "Spheroidal aggregate culture of rat liver cells: histotypic reorganization, biomatrix deposition, and maintenance of functional activities" J Cell Biol 1985; 101:914-923.
Lin et al., "La2Zr2O7 and MgO co-doped composite Li-Garnet solid electrolyte", Journal of Energy Chemistry, vol. 40, 2020, pp. 132-136.
Liquid Surge Control, LLC; "The Latest in Drop-In Baffle Technology"; 2 Pages; (2019).
Lonza Inc., "SeaPrep Agarose: An Ultralow Gelling, Soft Agarose", Available Online at <http://www.lonzabio.jp/catalog/pdf/pd/PD031.pdf>, 2007, pp. 1-4.
Lovett et al. "Vascularization Strategies for Tissue Engineering" Tissue Engineering Part B, 2009, vol. 15, No. 3, pp. 353-370.
Lquid Surge Control, LLC; "The Latest in Drop-In Baffle Technology"; 2 Pages; (2019).
Martin et al., "Agarose and Methylcellulose Hydrogel Blends for Nerve Regeneration Applications", J. Neural Eng., vol. 5, 2008, pp. 221-231.
McMillan, "Shear stress in microfluidic devices" Darwin Microfludics interner article (Year: 2017).
Messner et al, Multi-cell type human liver microtissues for hepatotoxicity testing. Archives of Toxicology, Nov. 11, 2012, 5 pages.
Mimetas The Organ-on-a-Chip Company; "Organ-on-a-Chip Models for Science and Pharma"; 4 Pages; (Downloaded Mar. 9, 2020); https://mimetas.com/.
Curcio et al. "Mass transfer and metabolic reactions in hepatocyte spheroids cultured in rotating wall gas-permeable membrane system." Biomaterials 28 (2007) 5487-5497. (Year: 2007).
Evenou et al. "Spontaneous Formation of Highly Functional Three-Dimensional Multilayer from Human Hepatoma Hep G2 Cells Cultured on an Oxygen-Permeable Polydimethylsiloxane Membrane." Tissue Engineering: Part C vol. 16, No. 2, 2010, pp. 311-318. (Year: 2010).
Koike et al. "Characterization of Embryo id Bodies of Mouse Embryonic Stem Cells Formed under Various Culture Conditions and Estimation of Differentiation Status of Such Bodies." Journal of Bioscience and Bioengineering vol. I 04, No. 4, 294-299. 2007. (Year: 2007).
Nortis; "Bridging the Gap Between In Vitro and In Vivo Research"; 16 Pages; (2015); https://www.nortisbio.com/.
Office Action and Search Report for CN 201580071454.0 mailed Sep. 27, 2019; 8 pages; Chinese Patent Office.
Office Action dated Aug. 8, 2019 pertaining to U.S. Appl. No. 15/708,473, filed Sep. 19, 2017, 20 pgs.
Organovo, "Pioneering Bioprinted Tissues to Treat Disease"; 2 Pages; (Downloaded Mar. 9, 2020) http://organovo.com/.
Otsuka et al., "Two-dimensional multiarray formation of hepatocyte spheroids on a microfabricated PEG-brush surface." ChemBioChem 2004; 5:850-855.
Polyimide: Japan Polyimide and Aromatic Polymers Study Group, 2010, pp. 364-371 Table 2.
Rezende et al, "Scalable Biofabrication of Tissue Spheroids for Organ Printing"; Sciverse Science Direct, Procedia Cirp 5, (2013) 276-281.
Sakai et al, "Detachably Assembled Microfluidic Device for Perfusion Culture and Post-Culture Analysis of Spheroid Array"; Biotechnol. J. 2014, 9, 971-979.
Sakai et al, "Large-scale preparation and function of porcine hepatocyte spheroids." Int J Artif Organs 1996; vol. 19, No. 5, pp. 294-301.
Sakai et al, "Technique for the Control of Spheroid Diameter Using Microfabricated Chips"; ScienceDirect, Acta Biomaterialia 3 (2007) 1033-1040.
Sakai et al; "Technique for the Control of Spheroid Diameter Using Microfabricated Chips"; Sciencedirect, Acta Biomaterials 3 (2007) 1033-1040.
Satoh et al, "A Pneumatic Pressure-Driven Multi-Throughput Microfluidic Circulation Culture System" Lab Chip, 2016, 16, 2339-2348.
Second Office Action and Search Report for CN 201580071454.0 mailed Aug. 31, 2020; 8 pages.
Singapore Patent Application No. 11201703494P Examination Report dated Sep. 25, 2020; 5 Pages; Singapore Patent Office.
Singapore Patent Application No. 11201703500X, Office Action dated Mar. 9, 2021; 8 pages; Singapore Patent Office.
Singaporean Patent Application No. 11201703498W, Notice of Allowance dated Apr. 27, 2021, 4 pages (Original Document Only), Singaporean Patent Office.
Stemcell Technologies, Reproducible and Uniform Embryoid Bodies Using AggreWell Plates, StemCell Technologies, Version 3.0.0, Mar. 2011, Catalog #29146, pp. 1-28.
Tara; "Innovating Predictive Cardiac Physiology"; 4 Pages; (2019) http://tarabiosystems.com/.
The Lab Depot(Registered) Products for Discovery Lab Supplies; Shake Flasks, 3 and 4 Baffles Product Information; 5 Pages (2019).
Tissue Dynamics, "Disruptive Drug Development"; 3 Pages; (Downloaded Mar. 9, 2020); https://www.tissuedynamics.com/.
Tissue; Technology, Available on (https://www.tissuse.com/en/technology/), Accessed May 11, 2021, 4 pages.
Tobe et al, "Receptor-mediated formation of multilayer aggregates of primary cultured adult rat hepatocytes on tactose-subsliluled polystyrene" Biochem Biophys Res Commun 1992; 184(1):225-230.
Tong et al, "Long-term culture of adult rat hepatocyte spheroids." Exp Cell Res 1992; 200:326-332.
Tung et al, "High-throughput 3D spheroid culture and drug testing using 384 hanging drop array" Analyst, 2011, 136 (3), 473-478.
Weegman et al, "Nutrient Regulation by Continuous Feeding Removes Limitations on Cell Yield in the Large-Scale Expansion of Mammalian Cell Spheroids"; PLoS ONE, 2013, vol. 8, Issue 10, e76611, 10 Pages.

(56) References Cited

OTHER PUBLICATIONS

Wikipedia, "Antiroll Tanks"; 3 Pages; Page Last Edited May 23, 2019.
WO-2008149039 translation (Year: 2008).
Wrighton et al, "Forces of Change: Mechanics Underlying Formation of Functional 3D Organ Buds" Cell Stem Cell, May 7, 2015; 16(5): 453-454.
Xu et al, "Characterisation of some cytotoxic endpoints using rat liver and HepG2 spheroids as in vitro models and their application in hepatotoxicity studies. I. Glucose metabolism and enzyme release as cytotoxic markers." Toxicol Appl Pharmacol 2003; 189:100-111.
Yamada et al, "Efficient induction of hepatocyte spheroids in a suspension culture using a water-soluble synthetic polymer as an artificial matrix." J Biochem 1998; 123:1017-1023.
Yang et al.,"An Agarose-Gel Based Method for Transporting Cell Lines", Current Chemical Genomics, vol. 3, Jan. 2009, pp. 50-53.
Zuidema et al., "Fabrication and Characterization of Tunable Polysaccharide Hydrogel Blends for Neural Repair", Acta Biomaterialia, vol. 7, No. 4, Apr. 2011, pp. 1634-1643.
"Laboratory Flasks Selection Guide: Types, Features, Applications", Engineering360, <https://www.globalspec.com/learnmore/labware_scientific_instruments/labware_consumables/laboratory_flasks#:~:text=Laboratory%20flasks%20are%20lab%20vessels,the%20opening%20at%20the%20neck.> accessed Apr. 8, 2022 (Year: 2022).
Achilli et al., "Advances in the Formation, Use and Understanding of Multi-cellular Spheroids", Expert Opinion on Biological Therapy, vol. 12, No. 10, Jul. 2012, pp. 1347-1360.
Alepee et al, "State-of-the-Art 3D Cultures (Organs-on-a-Chip) in Safety Testing and Pathophysiology"; Transatlantic Think Tank for Toxicology, T4 Workshop Report, Altex 31, 4/14, pp. 441-477, Retrieved From: http://dx.doi.org/10.14573/altex1406111 (Jul. 14, 2014).
Aline, "We Engineer Microfluidic Products" ; 7 Pages; (2020) https://alineinc.com/.
AxoSIM, Nerve-on-a-Chip Mini-Brain About Team; 6 Pages; (Downloaded Mar. 9, 2020); http://axosim.com/.
BioIVT Elevating SCIENCE(Registered); 6 Pages; (2020); http://www.hepregen.com/.
Brandrup et al., "Polymer Handbook", Fourth Edition, Wiley-Interscience Publication, , Permeability and diffusion data, 1999, 9 pages (Contributors; Preface).
Cheng et al, "MicroRNA-34a Targets Forkhead Box J2 to Modulate Differentiation of Endothelial Progenitor Cells in Response to Shear Stress", J Mol Cell Cardiol. 74 (2014) 4-12.
Chinese Patent Application No. 201580071454.0 First Office Action dated Sep. 27, 2019, 23 pages Chinese Patent Office.
Chinese Patent Application No. 201580071454.0 Office Action dated Aug. 31, 2020; 8 Pages; Chinese Patent Office.
Chinese Patent Application No. 201580071507.9 Office Action dated Sep. 1, 2020; 20 Pages; Chinese Patent Office.
Chinese Patent Application No. 201580071507.9, Office Action dated Mar. 29, 2021, 8 pages (English Translation Only), Chinese Patent Office.
Chinese Patent Application No. 201580071527.6 Office Action dated Aug. 31, 2020; 19 Pages; Chinese Patent Office.
CN-Bio, "Transforming Drug Discovery and the Lives of Patients"; 5 Pages; (2020) http:/cn-bio.com/.
Colazzo et al, "Shear Stress and VEGF Enhance Endothelial Differentiation of Human Adipose-Derived Stem Cells", Growth Factors, 2014, 32(5):139-149.
Corning Life Sciences Product Portfolio; 5 Pages Saved Mar. 6, 2020.
Corning(Registered) HTS Transwell(Registered)—96 Tissue Culture Systems, Permeable Supports for High Throughput Screening Applications; 2 Pages (2004).
Document entitled Description EP2653531A1, machine translation of EP 2653531 A1 provided by Proquest, original document published 2013 (Year: 2013).
Domansky et al, "Perfused Multiwell Plate for 30 Liver Tissue Engineering", Lab Chip, 2010, 10:51-58.
ELVEFLOW; "Microfluidics Innovation Center"; 6 Pages; (Downloaded Mar. 9, 2020); https://www.elveflow.com.
Emulate, 6 Pages; (2019) https://emulatebio.com/.
Endo et al., "Gene transfection to spheroid culture system on micropatterned culture plate by polyplex nanomicelle: a novel platform of genetically-modified cell transplantation", Drug Deliv. and Transl. Res., 2012, vol. 2, p. 398-405.
Engelberg et al, "Essential operating principles for tumor spheroid growth", BMC Systems Biology 2008, 2:110, 19 pages.
European Patent Application No. 15794415.8 Office Action dated Dec. 13, 2018; 4 Pages; European Patent Office.
European Patent Application No. 18749241.8 Communication pursuant to Article 94(3) EPC dated Oct. 23, 2020; 3 Pages; European Patent Office.
European Patent Application No. 14727673.7 Communication pursuant to Article 94(3) EPC Mailed Mar. 25, 2019; 6 pages; European Patent Office.
European Patent Application No. 14727673.7 Communication under Rule 71(3) EPC dated Jul. 24, 2019; 6 pages; European Patent Office.
European Patent Application No. 14727673.7 Decision to grant a European patent; dated Dec. 12, 2019; 2 pages; European Patent Office.
European Patent Application No. 14727673.7; Communication pursuant to Article 94(3) EPC dated Aug. 6, 2018; 5 pages; European Patent Office.
European Patent Application No. 15791186.8 Office Action dated Nov. 20, 2018; 4 Pages; European Patent Office.
European Patent Application No. 15791189.2 Communication pursuant to Article 94(3) EPC dated Nov. 29, 2018; 3 Pages; European Patent Office.
European Patent Application No. 15791194.2 Communication pursuant to Article 94(3) EPC dated Nov. 22, 2018; 3 Pages: European Patent Office.
European Patent Application No. 15793987.7 Office Action dated Dec. 13, 2018; 4 Pages; European Patent Office.
European Patent Application No. 18749240.0 Communication under Rule 71(3) EPC dated Mar. 11, 2021; 6 Pages; European Patent Office.
European Patent Application No. 18749241.8 Communication pursuant to Article 94(3) EPC dated Oct. 8, 2020; 3 Pages; European Patent Office.
European Patent Application No. 18749241.8 Office Action dated Mar. 12, 2021; 5 Pages; European Patent Office.
European Patent Application No. 18749265.7 Office Action dated Nov. 17, 2020; 4 pages; European Patent Office.
European Patent Application No. 18749948 Communication pursuant to Article 94(3) EPC dated Dec. 16, 2020; 5 Pages; European Patent Office.
European Patent Application No. 18749949.6 Communication from the Examining Division dated Jun. 1, 2021; 2 Pages; European Patent Office.
European Patent Application No. 18749949.6 Office Action dated Nov. 17, 2020; 4 pages; European Patent Office.
European Patent Application No. 18749952.0 Office Action dated Nov. 17, 2020; 4 pages; European Patent Office.
European Patent Application No. 18749953 Communication pursuant to Article 94(3) EPC dated Dec. 17, 2020; 4 Pages; European Patent Office.
Extended Partial European Search Report and Search Opinion; 19211588.9; Mailed Mar. 10, 2020; 11 pages; European Patent Office.
Fukuda et al, "Efficacy of a polyurethane foam/spheroid artificial liver by using human hepaloblastoma cell line (Hep G2)", Cell Transplantation, 2003, 12:51-58.
G-Plate: Accelerate your cell cultures to the next dimension, "An original cell culture model allowing for inland shaped 3D cell aggregates" 1 page, retrieved Sep. 8, 2015.
GeoCHEM Incorporated, Product Line; hllps://www.geocheminc.com, 4 Pages; (2020).

(56) References Cited

OTHER PUBLICATIONS

HμREL (Registered) Corporation, Bioanalytic Tools Company; 2 Pages; (2013); http://hurelcorp.com/.

Haycock, "3D cell culture: a review of current approaches and techniques", Methods Mol Biol, 2011; 695:1-15.

Hsiao et al., "Effects of 3D Microwell Culture on Initial Fate Specification in Human Embryonic Stem Cells", Published in final edited form as AlChE J. vol. 60 No. 4, Apr. 2014, pp. 1225-1235.

Huang et al., "Preparation of dense Ta-LLZO/MgO composite Li-ion solid electrolyte: Sintering, microstructure, performance and the role of MgO", Journal of Energy Chemistry, vol. 39, 2019, pp. 8-16.

\* cited by examiner 114   115

114
   115

119   117

115

115

115

115

MICROWELL DESIGN AND FABRICATION FOR GENERATION OF CELL CULTURE AGGREGATES

This application is a continuation of U.S. patent application Ser. No. 15/499,370 filed on Apr. 27, 2017, which is a continuation of International Application Ser. No. PCT/US15/58123, filed on Oct. 29, 2015, which claims benefit of priority to U.S. Provisional Application Ser. No. 62/072,019 filed on Oct. 29, 2014 the contents of which are relied upon and incorporated herein by reference in their entirety.

FIELD

The present disclosure relates to apparatuses, systems and methods for culturing cells.

TECHNICAL BACKGROUND

Cell culture techniques that encourage formation of 3D aggregates or spheroids have been strongly advocated over traditional monolayer culture techniques due to the increased number of applications. However, some conventional cell culture apparatuses currently used in forming spheroids make imaging techniques difficult.

BRIEF SUMMARY

In accordance with various embodiments of the present disclosure, apparatuses having wells for use in culturing cells to promote the formation of spheroids are described herein. Embodiments of apparatuses described herein have well geometries which minimize light distortion that can occur in conventional apparatuses used for culturing spheroids, allowing for improved imaging quality of spheroids grown in the wells.

In various embodiments, the disclosure describes a cell culture apparatus having a substrate defining a well. The well defines an interior surface, an exterior surface, an upper aperture and a nadir. The substrate defines a thickness between the interior surface and the exterior surface. A thickness of the substrate proximate to the nadir is greater than or equal to a thickness of the substrate proximate to the upper aperture.

In various embodiments, the disclosure describes a cell culture apparatus including a reservoir comprising a bottom and an enclosing sidewall. The bottom is defined by a plurality of wells. Each well of the plurality of wells defines an interior surface, an exterior surface, an upper aperture and a nadir. The well defines a thickness between the interior surface and the exterior surface. A thickness of the well proximate to the nadir is greater than or equal to a thickness of the well proximate to the upper aperture.

In various embodiments, the disclosure describes a cell culture apparatus including a substrate defining a well. The well defines an interior surface, an exterior surface, an upper aperture and a nadir. The substrate defines a thickness between the interior surface and the exterior surface. The thickness is configured to correct for refraction of light passing into the interior surface and out of the exterior surface when the well contains a water-based composition. In embodiments, the water-based composition is a composition employed in cell culture or cell assays. For example, a water-based composition can include a cell culture medium, buffers or other solutions or mixtures employed in cell assays.

In various embodiments, the disclosure describes a cell culture apparatus includes a substrate defining a well. The well defines an interior surface, an exterior surface, an upper aperture and a nadir. A shape of the exterior surface is configured to correct for refraction of light passing into the interior surface and out of the exterior surface.

In some embodiments, provided herein is a cell culture apparatus comprising: a substrate defining a well, wherein the well defines an interior surface, an exterior surface, an upper aperture and a nadir, wherein the substrate defines a thickness between the interior surface and the exterior surface, wherein a thickness of the substrate proximate to the nadir is greater than or equal to a thickness of the substrate proximate to the upper aperture. In some embodiments, the thickness of the substrate proximate to the nadir is greater than the thickness of the substrate proximate to the upper aperture. In some embodiments, the thickness of the substrate increases continuously from proximate the upper aperture to the nadir. In some embodiments, the thickness of the substrate proximate to the nadir is equal to the thickness of the substrate proximate to the upper aperture. In some embodiments, the thickness of the substrate remains constant from proximate the upper aperture to the nadir.

In some embodiments, the well defines an axis between the nadir and a center of the upper aperture, wherein the well is rotationally symmetrical about the axis.

In some embodiments, the upper aperture defines a distance across the upper aperture, wherein the distance across the upper aperture is in a range from 100 micrometers to 3000 micrometers.

In some embodiments, the thickness of the substrate at any location from proximate the upper aperture to the nadir is in a range from 10 micrometers to 1000 micrometers.

In some embodiments, the interior surface is defined by a hemispherical shape, wherein the hemispherical shape defines a radius in a range from 50 micrometers to 1500 micrometers.

In some embodiments, the exterior surface is configured to transmit light with a divergent angle smaller than the numerical aperture of the imaging system. For example for 4× Plan Achromat magnification objective with numerical aperture 0.1, light should pass substantially parallel (i.e., 5.7° or less) to a direction that the light was received by the interior surface when the well contains a cell culture medium. In general, the maximum divergence angle of the light passing through the well with cell culture should not exceed the acceptance cone of an objective.

In some embodiments, the shape of the interior surface and the shape of the exterior surface are configured to minimize refraction of light that passes there between when the well contains a cell culture medium.

In some embodiments, the well is non-adherent to cells.

In some embodiments, the interior surface is configured such that cells cultured therein form a spheroid.

Also provided herein is a cell culture apparatus comprising: a reservoir comprising a bottom and an enclosing sidewall, wherein the bottom is defined by a plurality of wells, wherein each well of the plurality of wells defines an interior surface, an exterior surface, an upper aperture and a nadir, wherein the well defines a thickness between the interior surface and the exterior surface, wherein a thickness of the well proximate to the nadir is greater than or equal to a thickness of the well proximate to the upper aperture.

Further provided herein is a cell culture apparatus comprising: a substrate defining a well, wherein the well defines an interior surface, an exterior surface, an upper aperture and a nadir, wherein the substrate defines a thickness between the interior surface and the exterior surface, wherein the thickness is configured to correct for refraction of light passing into the interior surface and out of the exterior surface when the well contains a water-based composition.

Further provided herein is a cell culture apparatus comprising: a substrate defining a well, wherein the well defines an interior surface, an exterior surface, an upper aperture and a nadir, wherein a shape of the exterior surface is configured to correct for refraction of light passing into the interior surface and out of the exterior surface.

Further provided herein are uses of any of the above for the growth and/or imaging or assessment of cells (e.g., spheroids).

Additional features and advantages of the subject matter of the present disclosure will be set forth in the detailed description which follows, and in part will be readily apparent to those skilled in the art from that description or recognized by practicing the subject matter of the present disclosure as described herein, including the detailed description which follows, the claims, as well as the appended drawings.

It is to be understood that both the foregoing general description and the following detailed description present embodiments of the subject matter of the present disclosure, and are intended to provide an overview or framework for understanding the nature and character of the subject matter of the present disclosure as it is claimed. The accompanying drawings are included to provide a further understanding of the subject matter of the present disclosure, and are incorporated into and constitute a part of this specification. The drawings illustrate various embodiments of the subject matter of the present disclosure and together with the description serve to explain the principles and operations of the subject matter of the present disclosure. Additionally, the drawings and descriptions are meant to be merely illustrative, and are not intended to limit the scope of the claims in any manner.

BRIEF DESCRIPTION OF THE DRAWINGS

The following detailed description of specific embodiments of the present disclosure can be best understood when read in conjunction with the following drawings, where like structure is indicated with like reference numerals and in which.

DETAILED DESCRIPTION

Figure 1:
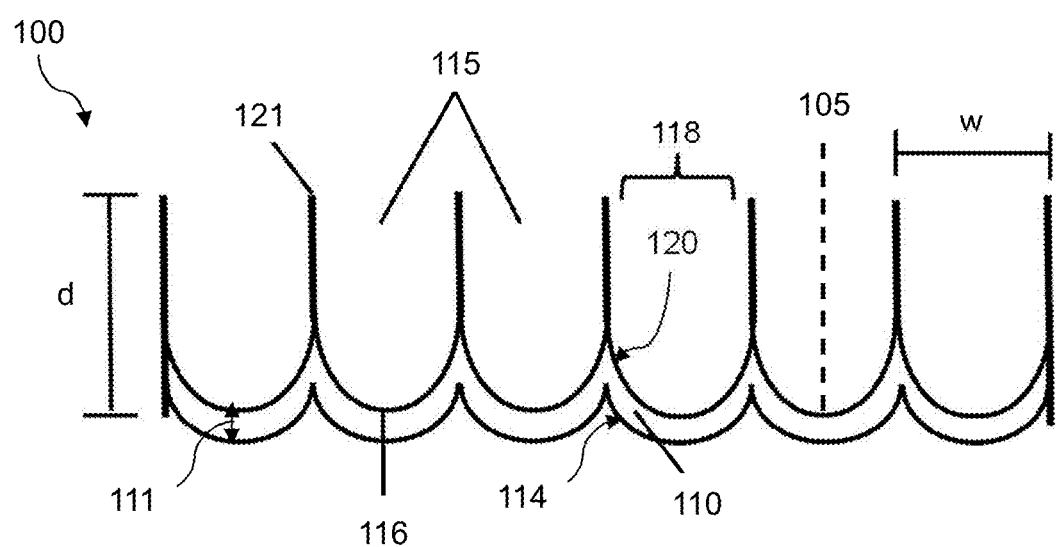
FIG. 1 is a schematic cross-sectional view of an embodiment of a cell culture apparatus including a plurality of wells.

Reference will now be made in greater detail to various embodiments of the subject matter of the present disclosure, some embodiments of which are illustrated in the accompanying drawings. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar to other numbered components.

The present disclosure describes, among other things, cell culture apparatuses having a structured bottom surface defining a shape of a plurality of wells or microwells. In some embodiments, a substrate forming the wells can comprise an exterior surface that defines an external surface of the apparatus. The shape of the external surface can be controlled to facilitate imaging of cells within the wells in accordance with various embodiments described herein.

In some embodiments, the wells may be configured such that cells cultured in the wells form spheroids. For example, the wells may be non-adherent to cells to cause the cells in the wells to associate with each other and form spheres. The spheroids may expand to size limits imposed by the geometry of the cells. In some embodiments, the wells may be coated with an ultra-low binding material to make the wells non-adherent to cells.

In some embodiments, the inner surface of the wells may be non-adherent to cells. The wells may be formed from non-adherent material or may be coated with non-adherent material to form a non-adherent well. In some embodiments, the non-adherent material may be described as an ultra-low-adhesion material. Examples of non-adherent material include perfluorinated polymers, olefins, or like polymers or mixtures thereof. Other examples may include agarose, non-ionic hydrogels such as polyacrylamides, or like materials or mixtures thereof. The combination of, for example, non-adherent wells, well geometry, and gravity may induce cells cultured in the wells to self-assembly into spheroids.

However, well geometries that can be useful for culturing spheroids can be difficult to image, either manually or via automated processes, with conventional microscopy techniques due to light distortions introduced through lens like effects by each individual well.

The well or well array design described herein may make image analysis of in vitro 3-dimensional spheroid based assays or spheroid production possible or more feasible. The cross-sectional profile of an individual well may have an impact on quality of imaging capabilities, e.g., microscope imaging capabilities. Specifically, controlling the well thickness and outer shape of the well may help compensate for light path deviation during imaging to improve image quality and may make the cell culture system amenable to high content imaging screening. As a result, the well thickness and outer shape of the well may lead to a well that is optically active due to the lens shape. In other words, the well may be able to utilize one or a variety of light sources and still produce uniform illumination of the cells in the well. In some embodiments, an improved illumination may allow for a shorter focal length, which may increase the NA of the system and allow image acquisition at higher magnifications.

A variety of well characteristics may have a significant impact on imaging quality. For example, dimensions and shape of an interior surface of the well, dimensions and shape of an exterior surface of the well, optical properties of the material defining the well, the thickness profile of the material defining the well, etc. can all play a role in high quality microscopy imaging. Additionally, the refractive index of a material may have a significant impact on imaging quality in both reflective and transmittance microscopy applications. For example, in the case of many cell culture imaging applications, the most common material that is in contact with the interior surface of the well is a water-based solution with a refractive index of 1.33 and the most common material for the well fabrication is polystyrene with a refractive index of 1.59. The differences in refractive indexes of the two materials may cause any incident light beam to deflect/reflect and may result in a negative impact on the microscope image quality.

One way to improve the quality of cell culture images may be to correct the light distortion. The light distortion may be corrected by controlling and varying the well characteristics discussed above. Specifically, the dimensions and shape of the interior and exterior surfaces of the well and the thickness profile of the material defining the well. Previously published fabrication methods have focused on the dimensions and shape of the interior surface of the well, especially, the interior surface that defines the dimensions of the 3D cellular aggregates. However, adjusting any of these characteristics in relation to one another may help to compensate for any light distortion that may occur during imaging (e.g., microscopy, etc.). More specifically, and as described herein, the light distortion may be corrected by controlling the shape and dimensions of the exterior surface of the well. In other words, the ability to change the shape and dimensions of the exterior surface may be utilized to help control the angle at which incident light exits the exterior surface.

A cell culture apparatus 100 including a plurality of wells 115 is shown in FIG. 1. The plurality of wells 115 may be defined by a substrate 110, e.g., a polymeric material. Each well 115 may define an interior surface 120, an exterior surface 114, an upper aperture 118, a nadir 116, and an upper edge 121. The substrate 110 may define a thickness 111 between the interior surface 120 and the exterior surface 114. The wells 115 may have a depth d defined by a height from the nadir 116 to the upper aperture 118. The wells 115 may also have a diametric dimension w, such as a diameter, width, etc., across the well 115 defined by the upper aperture 118.

In some embodiments, the wells 115 described herein may define a diametric dimension w of about, e.g., greater than or equal to 100 micrometers, greater than or equal to 300 micrometers, greater than or equal to 500 micrometers, greater than or equal to 800 micrometers, greater than or equal to 1200 micrometers, etc. or, less than or equal to 3000 micrometers, less than or equal to 2600 micrometers, less than or equal to 2200 micrometers, less than or equal to 1800 micrometers, less than or equal to 1500 micrometers, etc., including ranges between any of the foregoing values. Such diametric dimensions can control the size of a spheroid grown therein such that cells at the interior of the spheroid are maintained in a healthy state. In some embodiments, the wells 115 may define a depth d, by way of example, greater than or equal to 100 micrometers, greater than or equal to 300 micrometers, greater than or equal to 500 micrometers, greater than or equal to 800 micrometers, greater than or equal to 1200 micrometers, etc. or, less than or equal to 3000 micrometers, less than or equal to 2600 micrometers, less than or equal to 2200 micrometers, less than or equal to 1800 micrometers, less than or equal to 1500 micrometers, etc., including ranges between any of the foregoing values. Of course, other suitable dimensions may also be employed.

The exterior surface of the well may be a variety of shapes. For example, the shape of the exterior surface may be configured to correct for refraction of light passing into the interior surface of the well and out of the exterior surface of the well or vice versa. In other words, the light passing out of the exterior surface of the well is substantially parallel to the light passing into the interior surface and/or the shape of the exterior surface may be configured to minimize refraction of light that passes between the interior and exterior surfaces and/or the exterior surface may be configured to transmit light substantially parallel to a direction that the light was received by the interior surface of the well. In some embodiments, the well contains a cell culture medium, and the shape of the exterior surface corrects for refraction.

The thickness of the substrate between the interior surface of the well and the exterior surface of the well may vary. For example, the thickness of the substrate may be configured to correct for refraction of light passing into the interior surface of the well and out of the exterior surface of the well or vice versa. In other words, the light passing out of the exterior surface of the well is substantially parallel to the light passing into the interior surface or the thickness of the substrate may be configured to minimize refraction of light that passes there between. In some embodiments, the well contains a cell culture medium when the thickness of the substrate corrects for refraction.

Figure 2A:
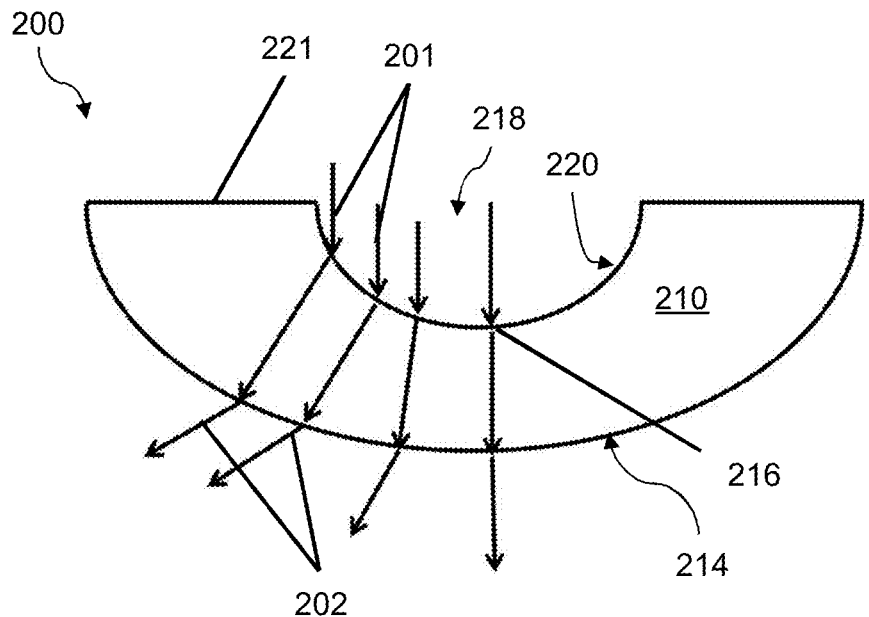
FIG. 2A is a cross-sectional view of an embodiment of one well of a cell culture apparatus.
Figure 2B:
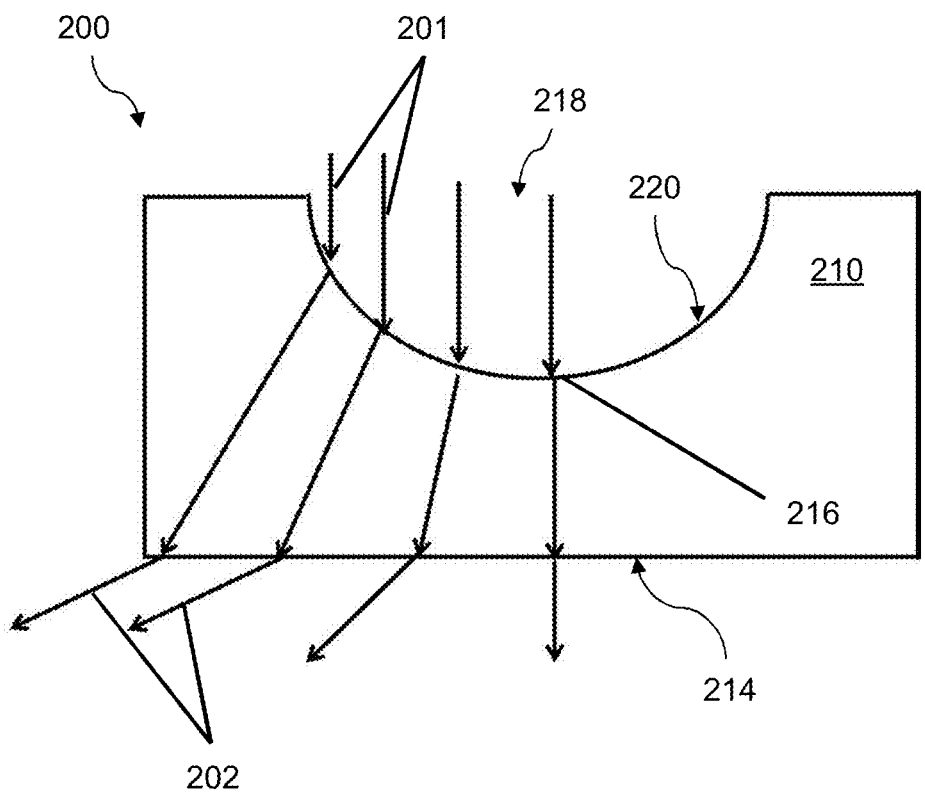
FIG. 2B is a cross-sectional view of an embodiment of one well of a cell culture apparatus.

The cross-sections of two wells 200 that define an exterior surface 214 that does not correct for refraction are shown in FIGS. 2A and 2B. In other words, light that enters 201 the interior surface 220 of the well 200 is not parallel with light that exits 202 the exterior surface 214 of the well 200.

As shown in FIG. 2A, the thickness of the substrate 210 proximate the nadir 216 is less than the thickness of the substrate 210 proximate the upper edge 221 of the well 200. The thickness of the substrate 210 proximate the upper edge 221 of the well 200 may be defined as a thickness between the interior surface 220 and the exterior surface 214 on a same plane as the upper aperture 218. As shown in FIG. 2B, the exterior surface 214 of the well 200 defines a rectangular shaped bottom of the substrate 210 that creates a flat exterior surface of the well 200.

Figure 3A:
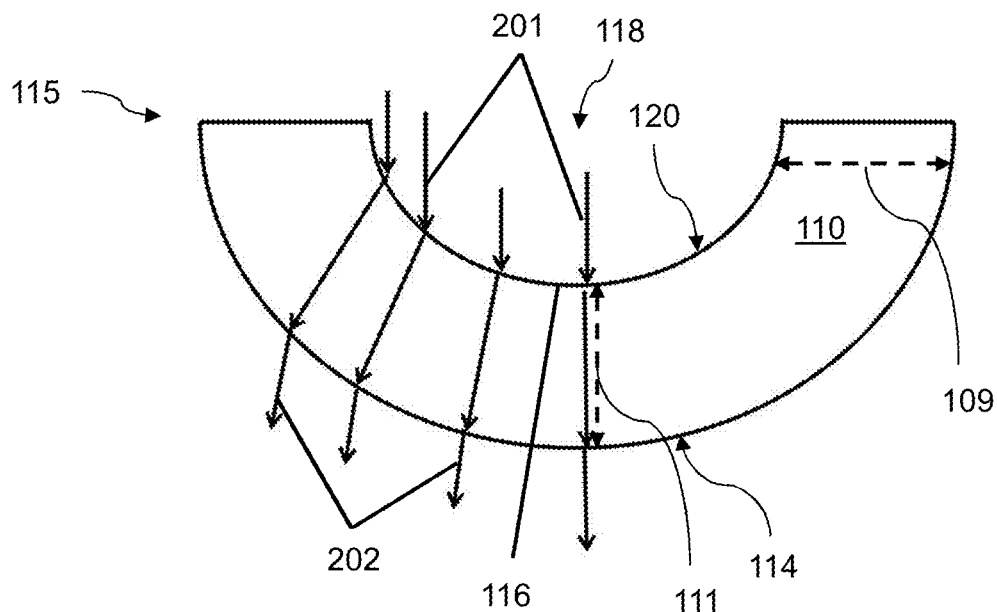
FIG. 3A is a cross-sectional view of an embodiment of one well of a cell culture apparatus.
Figure 3B:
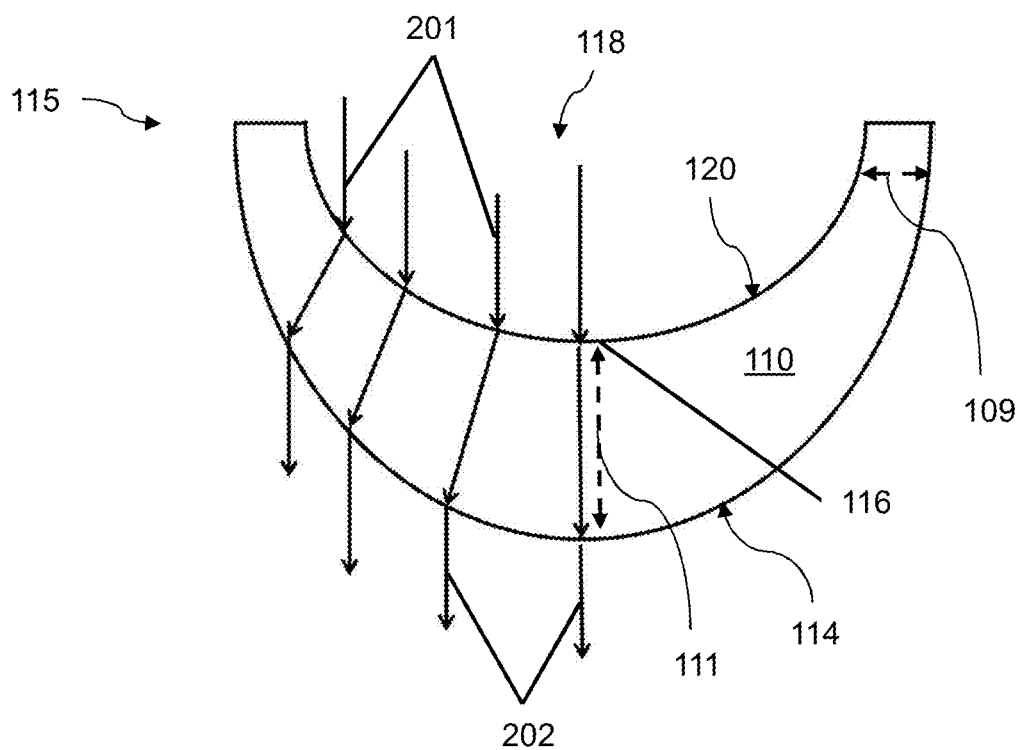
FIG. 3B is a cross-sectional view of an embodiment of one well of a cell culture apparatus.

In some embodiments, the thickness and shape of the substrate, e.g., a polymeric material, that defines the well may be configured to correct for refraction of light passing into the interior surface of the well and out of the exterior surface of the well. The cross-sections of two embodiments of wells 115 that define an exterior surface 114 that does correct for refraction are shown in FIGS. 3A and 3B. In other words, light that enters 201 the interior surface 120 of the well 115 is parallel with light that exits 202 the exterior surface 114 of the well 115. In yet other words, a shape of the interior surface 120 of the well 115 and a shape of the exterior surface 114 of the well 115 are configured to minimize the effects of the refraction of light that passes there between.

As shown in FIGS. 3A and 3B, the thickness 111 of the substrate 110 proximate the nadir 116 may be greater than or equal to the thickness 109 of the substrate 110 proximate the upper aperture 118. The thickness of the substrate 110 proximate the nadir 116 may be defined as a distance between the interior surface 120 and the exterior surface 114 at a lowest point of the well 115. The thickness of the substrate 110 proximate the upper aperture 118 may be defined as a thickness between the interior surface 120 and the exterior surface 114 on a same plane as the upper aperture 118.

Specifically, as shown in FIG. 3A, the thickness of the substrate 110 remains constant from proximate the upper aperture 118 to the nadir 116 and, as shown in FIG. 3B, the thickness 111 of the substrate 110 proximate the nadir 116 is greater than the thickness 109 of the substrate 110 proximate the upper aperture 118. Also, as shown in FIG. 3A, the thickness 111 of the substrate 110 proximate to the nadir 116 may be equal to the thickness 109 of the substrate 110 proximate the upper aperture 118. The substrate thicknesses shown in FIGS. 3A and 3B allow for an incoming light 201 entering the interior surface 120 to be substantially parallel to an outgoing light 202 leaving the exterior surface 114.

In other embodiments, the substrate thickness may be described as increasing continuously from proximate the upper aperture to the nadir (e.g., FIG. 3B). The thickness of the substrate proximate any location from the upper aperture to the nadir may be defined by a thickness of, e.g., greater than or equal to 5 micrometers, greater than or equal to 10 micrometers, greater than or equal to 20 micrometers, greater than or equal to 40 micrometers, greater than or equal to 60 micrometers, etc. or, less than or equal to 100 micrometers, less than or equal to 90 micrometers, less than or equal to 80 micrometers, less than or equal to 65 micrometers, less than or equal to 50 micrometers, etc., including ranges between any of the foregoing values. In some embodiments, the thickness is about 1000 micrometers or less. In some embodiments, the thickness is in a range from 10 micrometers to 1000 micrometers.

In some embodiments, the well may define an axis 105 between the nadir and a center of the upper aperture and the well may be rotationally symmetrical about the axis 105 (see, e.g., FIG. 1). For example, a hemispherical shape may define the well. The hemispherical shape may be defined by a radius of about, e.g., greater than or equal to 50 micrometers, greater than or equal to 150 micrometers, greater than or equal to 250 micrometers, greater than or equal to 400 micrometers, greater than or equal to 600 micrometers, etc. or, less than or equal to 1500 micrometers, less than or equal to 1300 micrometers, less than or equal to 1100 micrometers, less than or equal to 900 micrometers, less than or equal to 750 micrometers, etc.

Figure 4A:
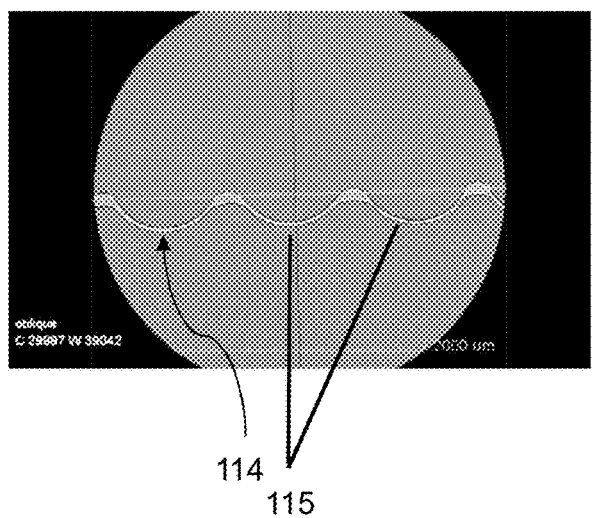
FIGS. 4A-4D are X-ray computed tomography images of the wells of FIG. 3A.
Figure 4B:
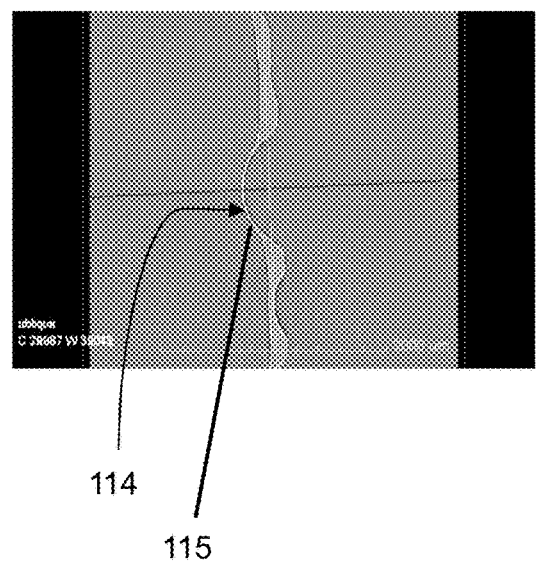
Figure 4C:
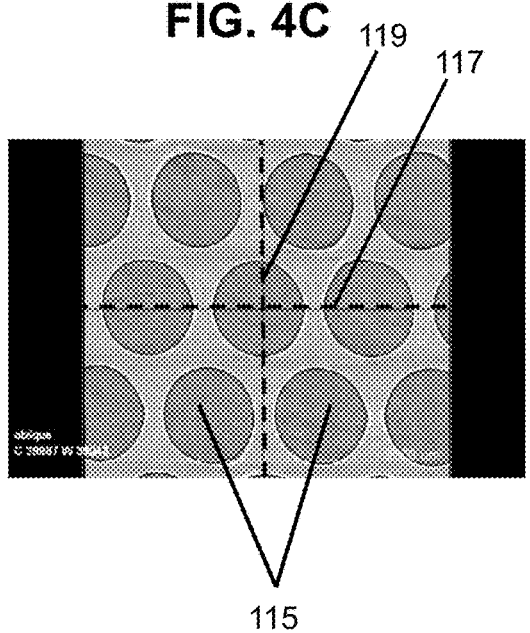
Figure 4D:
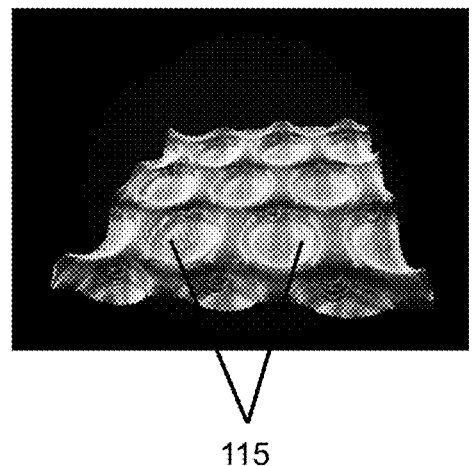

Orthogonal views of 3D datasets of X-ray computed tomography images of wells of generally as depicted in FIG. 3A are shown in FIGS. 4A-4D. The images depict wells 115 defining a convex exterior surface 114 as described in FIG. 3A. FIG. 4A depicts a cross sectional view of three complete wells 115 along horizontal line 117, shown in FIG. 4C. FIG. 4C is a top view of a portion of a cell culture apparatus with an array of wells 115. FIG. 4B is a cross sectional view of wells 115 along vertical line 119 shown in FIG. 4C. FIG. 4D is a reconstituted 3D image of a portion of a cell culture apparatus with an array of wells 115.

Figure 5A:
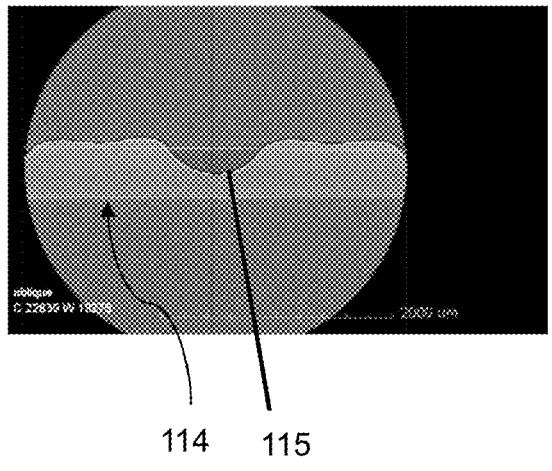
FIGS. 5A-5D are X-ray computed tomography images of the wells of FIG. 2B.
Figure 5B:
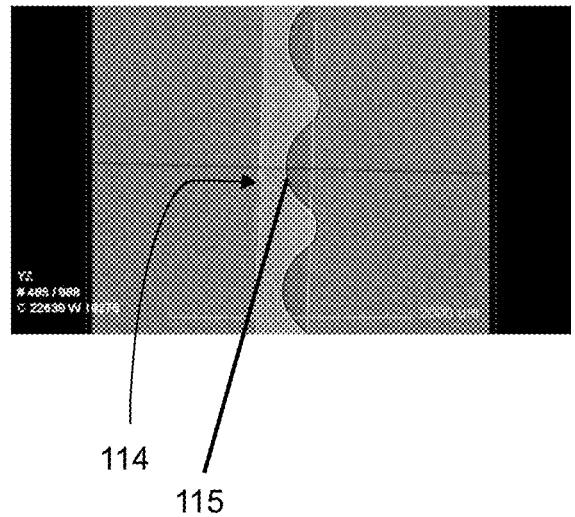
Figure 5C:
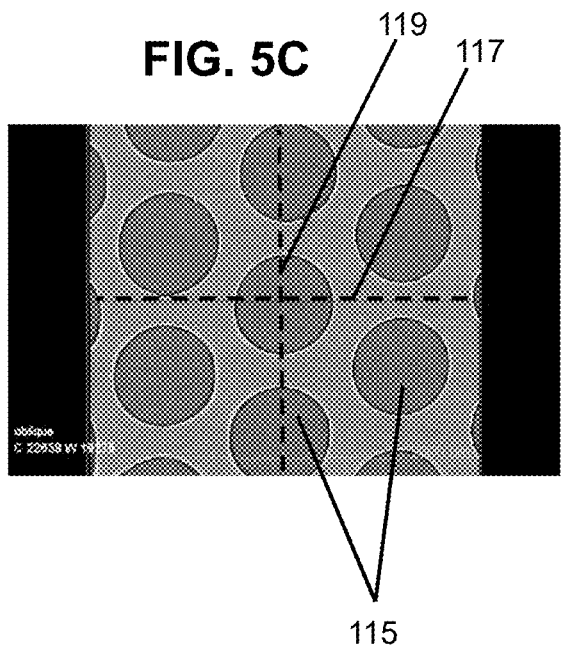
Figure 5D:
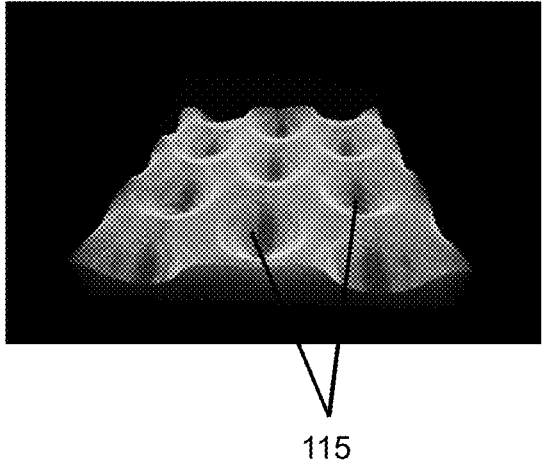

Orthogonal views of 3D datasets of X-ray computed tomography images of wells of generally as depicted in FIG. 2B are shown in FIGS. 5A-5D. The images depict wells 115 defining a flat exterior surface 114 as described in FIG. 2B. FIG. 5A depicts a cross sectional view of wells 115 along horizontal line 117 shown in FIG. 5C. FIG. 5C of a portion of a cell culture apparatus with an array of wells 115. FIG. 5B is a cross sectional view of wells 115 along vertical line 119 shown in FIG. 5C. FIG. 5D is a reconstituted 3D image of a portion of a cell culture apparatus with an array of wells 115.

Figure 6A:
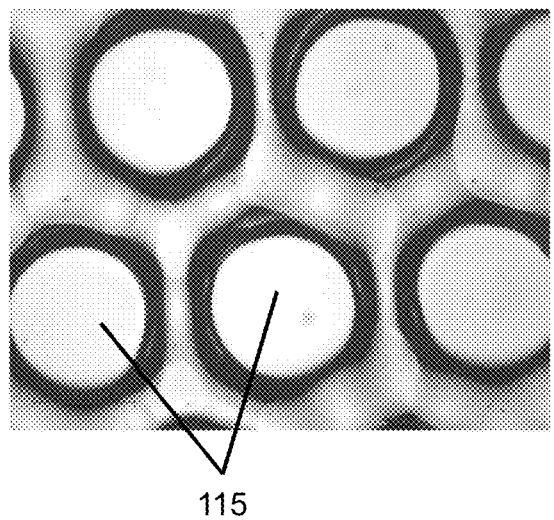
FIG. 6A is a bright field microscopy image of the wells of FIG. 3A.
Figure 6B:
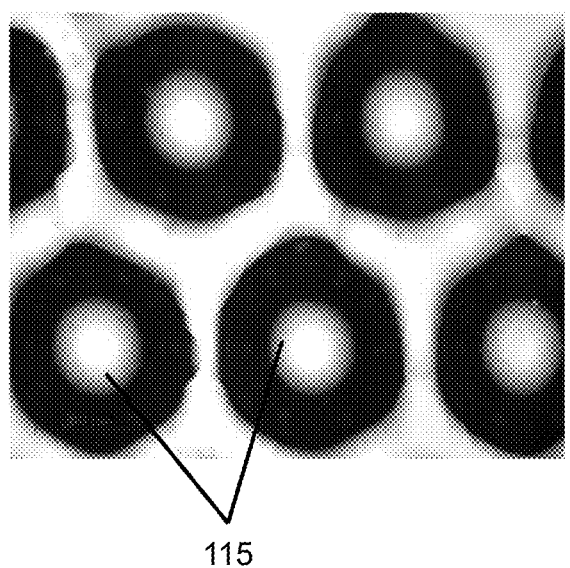
FIG. 6B is a bright field microscopy image of the wells of FIG. 2B.

Bright field microscopy images of wells 115 having shapes generally in accordance with FIGS. 3A and 2B are shown in FIGS. 6A and 6B, respectively. The microscopy images of FIG. 6A shows light that passed through wells having a shape as depicted in FIG. 3A. The microscopy images of FIG. 6B shows light that passed through wells having a shape as depicted in FIG. 2B. The shape of the well as depicted in FIG. 3A did not substantially reflect/deflect and thus yielded a relatively uniform signal across all wells as compared to the signal across wells having a shape as depicted in FIG. 2B. More light was received by the microscope camera for wells having a shape as depicted in FIG. 3A (see FIG. 6A) than the wells having a shape as depicted in FIG. 2B as shown in microscopy images of FIG. 6B. In other words, the well microscopy images of FIG. 6B depicts that more light was scattered, as shown by the dark rings, than the well microscopy images of FIG. 6A.

Figure 7:
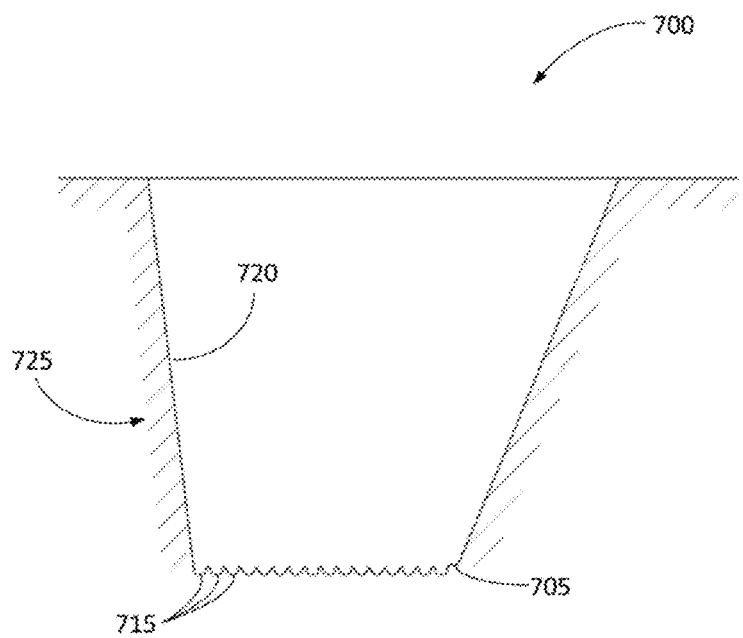
FIG. 7 is a schematic cross-sectional view of an embodiment of a reservoir including a plurality of wells.

As shown in FIG. 7, the cell culture apparatus 700 may include a reservoir 725.

The reservoir may include a bottom 705 and an enclosing sidewall 720. The bottom 705 may be defined by a plurality of wells 715. Each well 715 may have similar characteristics as wells described herein (see, e.g., FIGS. 1, 3A, and 3B).

In some embodiments, the exterior surface of the well is optimized through ray tracing for diffraction limited imaging performance when viewed under high resolution microscopy (e.g., bright field, fluorescence, confocal, or other microscopy modalities). For example, with reference to FIG. 2A and FIG. 2B, the exterior surface 214 is optimized through ray tracing.

To illustrate this approach, an interior surface of a polystyrene well may be a hemisphere with a radius of 500 micrometers and a center thickness of 150 micrometers. The diameter of a spheroid may be 300 micrometers, and a 20× microscope with an objective numerical aperture of 0.4 is employed. There may be a number of image points across positions of the spheroid, for example, center, 50 micrometers from the center, 100 micrometers from the center, and 150 micrometers from the center. In such instances, most images taken will be sub-optimum. Spot diagrams can be generated from the different field positions and compared to the diffraction limited Airy circle at the image plane to assess image quality. If the exterior surface is flat, as illustrated in FIG. 2B, the spot diameters across the field are a few times larger than the diffraction limit, indicating poor image quality. When the well has a uniform thickness, the image quality is considerably better than the previous case. However, diffraction limited imaging performance is barely achieved within the center 50 micrometer radius. Outside this field of view, astigmatism deteriorates the image quality. However, by optimizing the radius of curvature of the exterior surface to 0.518 mm, the image quality can achieve diffraction limited performance across the entire spheroid diameter, although a small amount of distortion and astigmatism still exist. To further optimize the image quality, an aspheric exterior surface is used. With a radius of curvature R=0.682 mm and a conic constant of K=−3.09, the residual aberration and distortion throughout the entire field of interest are removed. The conic surface is given by:

$$y^2 - 2Rx + (K+1)x^2 = 0.$$

Diffraction limited performance is also maintained in the entire volume of the spheroid. This enables high resolution confocal imaging in any locations within the spheroid. The actual magnification is 21.5× due to the refractive effect of the surface.

In some embodiments, nested wells are employed, whereby a first well or layer of wells is present above a second well or layer of wells. Well sidewalls of each well are selected such that light passing through two or more layers of wells remains substantially parallel to the original light.

Any suitable process can be used to fabricate cell culture apparatuses having wells as described herein. For example, a substrate can be molded to form the well or structured surface, a substrate film can be embossed to form the well or structured surface, or the like. In some embodiments, a deforming process is used to fabricate wells as described herein.

Figure 8:
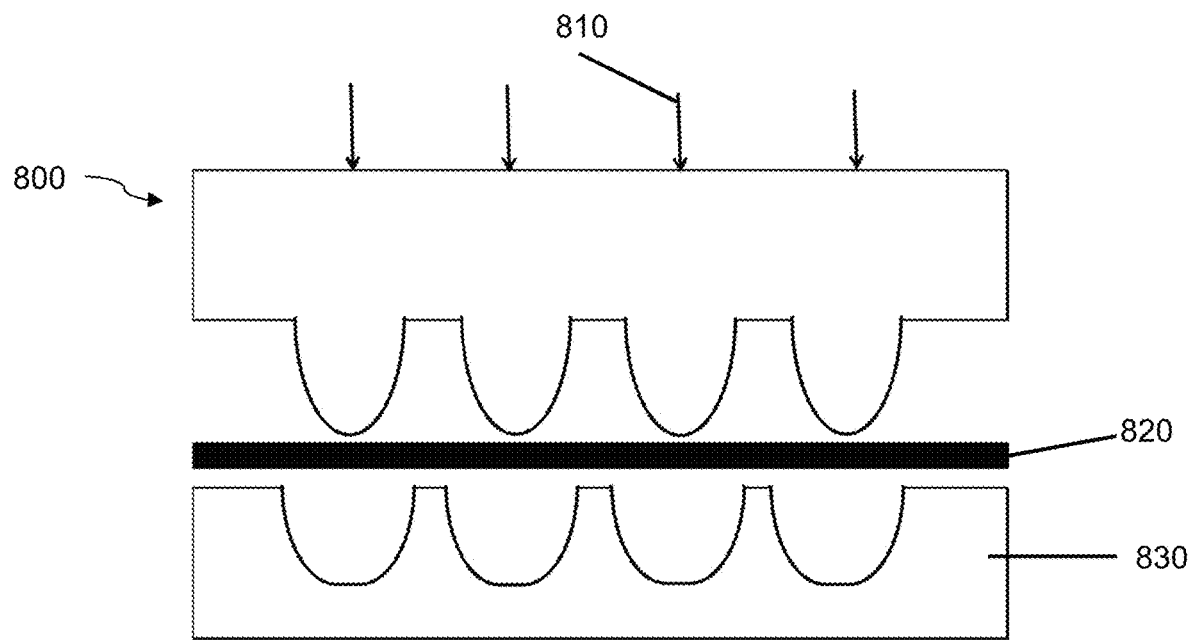
FIG. 8 is a schematic side view of a deforming process for fabrication of thin wall wells.

For example and with reference to FIG. 8, a schematic side view of a deforming process for fabrication of wells is shown. For example, FIG. 8 illustrates a hot embossing and film deforming process 800 for the fabrication of thin wall wells. The process uses a thin film 820 and applies heat and pressure 810 down onto the thin film 820 into the mold 830. The thin film 820 may have a specific thickness that results in a given thickness attributed to different sections of the wells. For example, a 70 micrometer thin film after going through a process of hot embossing and film deforming may have a uniform thickness of 25 micrometers at a bottom part of the well and upper part of the well. This outcome is similar to the well shown in FIG. 3A, which can sufficiently correct for light refraction. As a result, the hot embossing and film deforming process may be actively controlled during well fabrication to form wells that correct light refraction sufficiently similar to those in FIGS. 3A-3B. The well fabrication process may also be performed in planar configuration or as a roll to roll process.

Cell culture apparatuses having wells or structured surfaces as described herein can be formed from any suitable material. Preferably, materials intended to contact cells or culture media are compatible with the cells and the media. Typically, cell culture components (e.g., wells) are formed from polymeric material. Examples of suitable polymeric materials include polystyrene, polymethylmethacrylate, polyvinyl chloride, polycarbonate, polysulfone, polystyrene copolymers, fluoropolymers, polyesters, polyamides, polystyrene butadiene copolymers, fully hydrogenated styrenic polymers, polycarbonate PDMS copolymers, and polyolefins such as polyethylene, polypropylene, polymethyl pentene, polypropylene copolymers and cyclic olefin copolymers, and the like.

Cells cultured in three dimensions, such as spheroids, can exhibit more in vivo like functionality than their counterparts cultured in two dimensions as monolayers. In two dimensional cell culture systems, cells can attach to a substrate on which they are cultured. However, when cells are grown in three dimensions, such as spheroids, the cells interact with each other rather than attaching to the substrate. Cells cultured in three dimensions more closely resemble in vivo tissue in terms of cellular communication and the development of extracellular matrices. Spheroids thus provide a superior model for cell migration, differentiation, survival, and growth and therefore provide better systems for research, diagnostics, and drug efficacy, pharmacology, and toxicity testing.

In some embodiments, the devices are configured such that cells cultured in the devices form spheroids. For example, the wells in which cells are grown can be non-adherent to cells to cause the cells in the wells to associate with each other and form spheres. The spheroids expand to size limits imposed by the geometry of the wells. In some embodiments, the wells are coated with an ultra-low binding material to make the wells non-adherent to cells.

Examples of non-adherent material include perfluorinated polymers, olefins, or like polymers or mixtures thereof. Other examples include agarose, non-ionic hydrogels such as polyacrylamides, polyethers such as polyethylene oxide and polyols such as polyvinyl alcohol, or like materials or mixtures thereof. The combination of, for example, non-adherent wells, well geometry (e.g., size and shape), and/or gravity induce cells cultured in the wells to self-assemble into spheroids. Some spheroids maintain differentiated cell function indicative of a more in vivo-like, response relative to cells grown in a monolayer. Other cells types, such as mesenchymal stromal cells, when cultured as spheroids retain their pluripotency.

In some embodiments, the systems, devices, and methods herein comprise one or more cells. In some embodiments, the cells are cryopreserved. In some embodiments, the cells are in three dimensional culture. In some such embodiments, the systems, devices, and methods comprise one or more spheroids. In some embodiments, one or more of the cells are actively dividing. In some embodiments, the systems, devices, and methods comprise culture media (e.g., comprising nutrients (e.g., proteins, peptides, amino acids), energy (e.g., carbohydrates), essential metals and minerals (e.g., calcium, magnesium, iron, phosphates, sulphates), buffering agents (e.g., phosphates, acetates), indicators for pH change (e.g., phenol red, bromo-cresol purple), selective agents (e.g., chemicals, antimicrobial agents), etc.). In some embodiments, one or more test compounds (e.g., drug) are included in the systems, devices, and methods.

A wide variety of cell types may be cultured. In some embodiments, a spheroid contains a single cell type. In some embodiments, a spheroid contains more than one cell type. In some embodiments, where more than one spheroid is grown, each spheroid is of the same type, while in other embodiments, two or more different types of spheroids are grown. Cells grown in spheroids may be natural cells or altered cells (e.g., cell comprising one or more non-natural genetic alterations). In some embodiments, the cell is a somatic cell. In some embodiments, the cell is a stem cell or progenitor cell (e.g., embryonic stem cell, induced pluripotent stem cell) in any desired state of differentiation (e.g., pluripotent, multi-potent, fate determined, immortalized, etc.). In some embodiments, the cell is a disease cell or disease model cell. For example, in some embodiments, the spheroid comprises one or more types of cancer cells or cells that can be induced into a hyper-proliferative state (e.g., transformed cells). Cells may be from or derived from any desired tissue or organ type, including but not limited to, adrenal, bladder, blood vessel, bone, bone marrow, brain, cartilage, cervical, corneal, endometrial, esophageal, gastrointestinal, immune system (e.g., T lymphocytes, B lymphocytes, leukocytes, macrophages, and dendritic cells), liver, lung, lymphatic, muscle (e.g., cardiac muscle), neural, ovarian, pancreatic (e.g., islet cells), pituitary, prostate, renal, salivary, skin, tendon, testicular, and thyroid. In some embodiments, the cells are mammalian cells (e.g., human, mice, rat, rabbit, dog, cat, cow, pig, chicken, goat, horse, etc.).

The cultured cells find use in a wide variety of research, diagnostic, drug screening and testing, therapeutic, and industrial applications.

In some embodiments, the cells are used for production of proteins or viruses. Systems, devices, and methods that culture large numbers of spheroids in parallel are particularly effective for protein production. Three-dimensional culture allows for increased cell density, and higher protein yield per square centimeter of cell growth surface area. Any desired protein or viruses for vaccine production may be grown in the cells and isolated or purified for use as desired. In some embodiments, the protein is a native protein to the cells. In some embodiments, the protein is non-native. In some embodiments, the protein is expressed recombinantly. Preferably, the protein is overexpressed using a non-native promoter. The protein may be expressed as a fusion protein. In some embodiments, a purification or detection tag is expressed as a fusion partner to a protein of interest to facilitate its purification and/or detection. In some embodiments, fusions are expressed with a cleavable linker to allow separation of the fusion partners after purification.

In some embodiments, the protein is a therapeutic protein. Such proteins include, but are not limited to, proteins and peptides that replace a protein that is deficient or abnormal (e.g., insulin), augment an existing pathway (e.g., inhibitors or agonists), provide a novel function or activity, interfere with a molecule or organism, or deliver other compounds or proteins (e.g., radionuclides, cytotoxic drugs, effector proteins, etc.). In some embodiments, the protein is an immunoglobulin such as an antibody (e.g., monoclonal antibody) of any type (e.g., humanized, bi-specific, multi-specific, etc.). Therapeutic protein categories include, but are not limited to, antibody-based drugs, Fc fusion proteins, anticoagulants, antigens, blood factor, bone morphogenetic proteins, engineered protein scaffolds, enzymes, growth factors, hormones, interferons, interleukins, and thrombolytics. Therapeutic proteins may be used to prevent or treat cancers, immune disorders, metabolic disorders, inherited genetic disorders, infections, and other diseases and conditions.

In some embodiments, the protein is a diagnostic protein. Diagnostic proteins include, but are not limited to, antibodies, affinity binding partners (e.g., receptor-binding ligands), inhibitors, antagonists, and the like. In some embodiments, the diagnostic protein is expressed with or is a detectable moiety (e.g., fluorescent moiety, luminescent moiety (e.g., luciferase), colorimetric moiety, etc.).

In some embodiments, the protein is an industrial protein. Industrial proteins include, but are not limited to, food components, industrial enzymes, agricultural proteins, analytical enzymes, etc.

In some embodiments, the cells are used for drug discovery, characterization, efficacy testing, and toxicity testing. Such testing includes, but is not limited to, pharmacological effect assessment, carcinogenicity assessment, medical imaging agent characteristic assessment, half-life assessment, radiation safety assessment, genotoxicity testing, immunotoxicity testing, reproductive and developmental testing, drug interaction assessment, dose assessment, adsorption assessment, disposition assessment, metabolism assessment, elimination studies, etc. Specific cells types may be employed for specific tests (e.g., hepatocytes for liver toxicity, renal proximal tubule epithelial cells for nephrotoxicity, vascular endothelial cells for vascular toxicity, neuronal and glial cells for neurotoxicity, cardiomyocytes for cardiotoxicity, skeletal myocytes for rhabdomyolysis, etc.). Treated cells may be assessed for any number of desired parameters including, but not limited to, membrane integrity, cellular metabolite content, mitochondrial functions, lysosomal functions, apoptosis, genetic alterations, gene expression differences, and the like.

In some embodiments, the cell culture devices are a component of a larger system. In some embodiments, the system comprises a plurality (e.g., 2, 3, 4, 5, . . . , 10, . . . , 20, . . . , 50, . . . , 100, . . . , 1000, etc.) of such cell culture devices. In some embodiments, the system comprises an incubator for maintaining the culture devices at optimal culture conditions (e.g., temperature, atmosphere, humidity, etc.). In some embodiments, the system comprises detectors for imaging or otherwise analyzing cells. Such detectors include, but are not limited to, fluorimeters, luminometers, cameras, microscopes, plate readers (e.g., PERKIN ELMER ENVISION plate reader; PERKIN ELMER VIEWLUX plate reader), cell analyzers (e.g., GE IN Cell Analyzer 2000 and 2200; THERMO/CELLOMICS CELLNSIGHT High Content Screening Platform), and confocal imaging systems (e.g., PERKIN ELMER OPERA-PHENIX high throughput content screening system; GE INCELL 6000 Cell Imaging System). In some embodiments, the system comprises perfusion systems or other components for supplying, re-supplying, and circulating culture media or other components to cultured cells. In some embodiments, the system comprises robotic components (e.g., pipettes, arms, plate movers, etc.) for automating the handing, use, and/or analysis of culture devices.

All scientific and technical terms used herein have meanings commonly used in the art unless otherwise specified. The definitions provided herein are to facilitate understanding of certain terms used frequently herein and are not meant to limit the scope of the present disclosure.

As used herein, singular forms "a," "an" and "the" include plural referents unless the context clearly dictates otherwise. Thus, for example, reference to a "structured bottom surface" includes examples having two or more such "structured bottom surfaces" unless the context clearly indicates otherwise.

As used in this specification and the appended claims, the term "or" is generally employed in its sense including "and/or" unless the content clearly dictates otherwise. The term "and/or" means one or all of the listed elements or a combination of any two or more of the listed elements.

As used herein, "have", "has", "having", "include", "includes", "including", "comprise", "comprises", "comprising" or the like are used in their open ended inclusive sense, and generally mean "include, but not limited to", "includes, but not limited to", or "including, but not limited to".

"Optional" or "optionally" means that the subsequently described event, circumstance, or component, can or cannot occur, and that the description includes instances where the event, circumstance, or component, occurs and instances where it does not.

The words "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the inventive technology.

Ranges can be expressed herein as from "about" one particular value, and/or to "about" another particular value. When such a range is expressed, examples include from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

Also herein, the recitations of numerical ranges by endpoints include all numbers subsumed within that range (e.g., 1 to 5 includes 1, 1.5, 2, 2.75, 3, 3.80, 4, 5, etc.). Where a range of values is "greater than", "less than", etc. a particular value, that value is included within the range.

Any direction referred to herein, such as "top," "bottom," "left," "right," "upper," "lower," "above," below," and other directions and orientations are described herein for clarity in reference to the figures and are not to be limiting of an actual device or system or use of the device or system. Many of the devices, articles or systems described herein may be used in a number of directions and orientations. Directional descriptors used herein with regard to cell culture apparatuses often refer to directions when the apparatus is oriented for purposes of culturing cells in the apparatus.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that any particular order be inferred. Any recited single or multiple feature or aspect in any one claim can be combined or permuted with any other recited feature or aspect in any other claim or claims.

It is also noted that recitations herein refer to a component being "configured" or "adapted to" function in a particular way. In this respect, such a component is "configured" or "adapted to" embody a particular property, or function in a particular manner, where such recitations are structural recitations as opposed to recitations of intended use. More specifically, the references herein to the manner in which a component is "configured" or "adapted to" denotes an existing physical condition of the component and, as such, is to be taken as a definite recitation of the structural characteristics of the component.

While various features, elements or steps of particular embodiments may be disclosed using the transitional phrase "comprising," it is to be understood that alternative embodiments, including those that may be described using the transitional phrases "consisting" or "consisting essentially of," are implied. Thus, for example, implied alternative embodiments to a cell culture apparatus comprising a structured bottom surface, one or more sidewalls, a top and a port include embodiments where a cell culture apparatus consists of a structured bottom surface, one or more sidewalls, a top and a port and embodiments where a cell culture apparatus consists essentially of a structured bottom surface, one or more sidewalls, a top and a port.

It will be apparent to those skilled in the art that various modifications and variations can be made to the present inventive technology without departing from the spirit and scope of the disclosure. Since modifications, combinations, sub-combinations and variations of the disclosed embodiments incorporating the spirit and substance of the inventive technology may occur to persons skilled in the art, the inventive technology should be construed to include everything within the scope of the appended claims and their equivalents.

What is claimed is:

1. A cell culture apparatus comprising:
   a substrate defining a well, wherein the well comprises an interior surface having a hemispheric shape, an exterior surface having an aspheric a convex shape, an upper aperture and a nadir;
   wherein light passes between the interior surface and the exterior surface;
   wherein the substrate defines a thickness between the interior surface and the exterior surface;
   wherein the thickness increases continuously from proximate the upper aperture to the nadir; and
   wherein a majority of the well is fully illuminated when exposed to illumination with a brightfield microscope.

2. The cell culture apparatus of claim 1, wherein the thickness of the substrate proximate to the nadir is greater than the thickness of the substrate proximate to the upper aperture.

3. The cell culture apparatus of claim 1, wherein the well defines an axis between the nadir and a center of the upper aperture, wherein the well is rotationally symmetrical about the axis.

4. The cell culture apparatus according to claim 1, wherein the upper aperture defines a distance across the upper aperture, wherein the distance across the upper aperture is in a range from 100 micrometers to 3000 micrometers.

5. The cell culture apparatus according to claim 1, wherein the thickness of the substrate at any location from proximate the upper aperture to the nadir is in a range from 10 micrometers to 1000 micrometers.

6. The cell culture apparatus of claim 1, wherein the hemispherical shape of the interior surface defines a radius in a range from 50 micrometers to 1500 micrometers.

7. The cell culture apparatus according to claim 1, wherein the substrate comprises polystyrene.

8. The cell culture apparatus according claim 1, wherein the light entering the interior surface is substantially parallel to the light leaving the surface when the well contains a cell culture medium.

9. The cell culture apparatus according to claim 1, wherein a shape of the interior surface and a shape of the exterior surface are configured to minimize refraction of light that passes there between when the well contains a cell culture medium.

10. The cell culture apparatus according to claim 1, wherein the well is non-adherent to cells.

11. The cell culture apparatus according to claim 1, wherein the interior surface is configured such that cells cultured therein form a spheroid.

12. Use of the apparatus of claim 1 for the growth of a spheroid.

* * * * *